United States Patent
Seike et al.

(10) Patent No.: US 8,252,945 B2
(45) Date of Patent: Aug. 28, 2012

(54) PROTECTIVE AGENT FOR RETINAL NEURONAL CELL COMPRISING INDAZOLE DERIVATIVE AS ACTIVE INGREDIENT

(75) Inventors: Hisayuki Seike, Ikoma (JP); Takeshi Matsugi, Ikoma (JP); Atsushi Shimazaki, Ikoma (JP)

(73) Assignees: UBE Industries, Ltd., Yamaguchi (JP); Santen Pharmaceutical Co., Ltd., Osaka (JP)

( * ) Notice: Subject to any disclaimer, the term of this patent is extended or adjusted under 35 U.S.C. 154(b) by 1060 days.

(21) Appl. No.: 11/887,989

(22) PCT Filed: Apr. 12, 2006

(86) PCT No.: PCT/JP2006/307715
§ 371 (c)(1),
(2), (4) Date: Oct. 5, 2007

(87) PCT Pub. No.: WO2006/112313
PCT Pub. Date: Oct. 26, 2006

(65) Prior Publication Data
US 2009/0012123 A1    Jan. 8, 2009

(30) Foreign Application Priority Data
Apr. 13, 2005   (JP) .................................. 2005-116141

(51) Int. Cl.
*C07D 231/56* (2006.01)
*A61K 31/415* (2006.01)
(52) U.S. Cl. ..................... 548/361.1; 514/20.8; 514/394; 514/405
(58) Field of Classification Search ................. 514/20.8, 514/394, 405; 548/361.1
See application file for complete search history.

(56) References Cited

U.S. PATENT DOCUMENTS

| | | | |
|---|---|---|---|
| 4,599,353 | A | 7/1986 | Bito |
| 4,822,820 | A | 4/1989 | De Santis et al. |
| 5,773,471 | A | 6/1998 | Oguchi et al. |
| 5,877,211 | A | 3/1999 | Woodward |
| 5,886,035 | A | 3/1999 | Shirasawa et al. |
| 5,985,920 | A | 11/1999 | Shirasawa et al. |
| 2002/0025985 | A1 | 2/2002 | Ueno et al. |
| 2003/0105133 | A1 | 6/2003 | Bigge et al. |
| 2004/0102437 | A1 | 5/2004 | Takami et al. |

(Continued)

FOREIGN PATENT DOCUMENTS
EP    0 850 926 A2    7/1998
(Continued)

OTHER PUBLICATIONS

Kannabiran, Chitra, et al, "Genetics of Eye Disease," Journal of Genetics, vol. 88, No. 4, pp. 393-394 (Dec. 2009).*

(Continued)

*Primary Examiner* — Savitha Rao
(74) *Attorney, Agent, or Firm* — Holtz, Holtz, Goodman & Chick, P.C.

(57) ABSTRACT

As a result of intensive studies for the purpose of finding a new medicinal use of an indazole derivative, it was found that an indazole derivative inhibits glutamate-induced retinal neuronal cell death in rat fetal retinal neuronal cells, in other words, the indazole derivative acts directly on the retinal neuronal cells and exhibits an effect of protecting retinal neuronal cells. Accordingly, the indazole derivative is useful for the prevention or treatment of an eye disease associated with retinal neuronal cell damage or retinal damage.

5 Claims, 1 Drawing Sheet

U.S. PATENT DOCUMENTS

| | | | |
|---|---|---|---|
| 2004/0106646 A1 | 6/2004 | Takayama et al. | |
| 2004/0138286 A1 | 7/2004 | Imazaki et al. | |
| 2005/0026960 A1* | 2/2005 | Kephart et al. | 514/338 |
| 2007/0129404 A1* | 6/2007 | Hagihara et al. | 514/338 |

FOREIGN PATENT DOCUMENTS

| | | | |
|---|---|---|---|
| EP | 1 403 255 A1 | 3/2004 | |
| JP | 59-1418 A | 1/1984 | |
| JP | 3-501025 A | 3/1991 | |
| JP | 8-501310 A | 2/1996 | |
| JP | 9-87179 A | 3/1997 | |
| JP | 10-182465 A | 7/1998 | |
| JP | 10-251225 A | 9/1998 | |
| JP | 11-71344 A | 3/1999 | |
| JP | 10-259179 A | 9/1999 | |
| JP | 2001-072591 A | 3/2001 | |
| JP | 2001-523721 A | 11/2001 | |
| JP | 2002-293771 A | 10/2002 | |
| JP | 2003-146904 A | 5/2003 | |
| JP | 2003-527430 A | 9/2003 | |
| JP | 2003-321442 A | 11/2003 | |
| JP | 2004-2462 A | 1/2004 | |
| WO | WO 90/02553 A1 | 3/1990 | |
| WO | WO 94/06433 A1 | 3/1994 | |
| WO | WO 98/12175 A1 | 3/1998 | |
| WO | WO 01/56606 A1 | 8/2001 | |
| WO | WO 01/56988 A1 | 8/2001 | |
| WO | WO 02/22131 A1 | 3/2002 | |
| WO | WO 02/083175 A1 | 10/2002 | |
| WO | WO 02/100833 A1 | 12/2002 | |
| WO | WO 03/004058 A1 | 1/2003 | |
| WO | WO 2005/035506 A1 | 4/2005 | |
| WO | WO 2005035506 A1 * | 4/2005 | |

OTHER PUBLICATIONS

Naskar et al., Investigative Ophthalmology and visual science, 2002, vol. 43(9). 2962-2968.*

Mediterms Medical dictionary reference, Jun. 2004, downloaded from the internet on Oct. 20, 2011, URL: http://web.archive.org/web/20040626033308/http://www.medterms.com/script/main/art.asp?articlekey=22185.*

Kudo H. et al., "Latanoprost prevents retinal ganglion cell death induced by N-Methyl-D-Aspartate or optic nerve axotomy," *Invest. Ophthalmol. Vis. Sci.*, (2004), 45, Abstract 881, 881-B854.

Hayami Kayoko et al., "Photoreceptor Protection Against Constant Light-Induced Damage by Isopropyl Unoprostone, a Prostaglandin $F_{2\alpha}$ Metabolite-Related Compound," *Ophthalmic Research*, 2001, vol. 33, No. 4, pp. 203 to 209.

Drago, Filippo et al., "Latanoprost Exerts Neuroprotective Activity In Vitro and In Vivo," *Experimental Eye Research*, 2001, vol. 72, No. 4, pp. 479 to 486.

Yaniv Barkana et al., "Neuroprotection in Ophthalmology: A Review,", *Brain Research Bulletin*, 62, (2004), pp. 447 to 453.

Abbot F. Clark et al., "Ophthalmic Drug Discovery," *Nature Review*, vol. 2, (2003), pp. 448 to 459.

Kitaoka Y. et al., "Involvement of RhoA and possible neuroprotective effect of fasudil, a Rho kinase inhibitor, in NMDA-induced neurotoxicity in the rat retina," *Brain Research*, 20040820 NL, vol. 1018, No. 1, Aug. 20, 2004, pp. 111 to 118.

Monnier P.P. et al., "The Rho/ROCK pathway mediates neurite growth-inhibitory activity associated with the chondroitin sulfate proteoglycans of the CNS glial scar," *Molecular and Cellular Neuroscience*, 20030301 US, vol. 22, No. 3, Mar. 1, 2003, pp. 319 to 330.

* cited by examiner

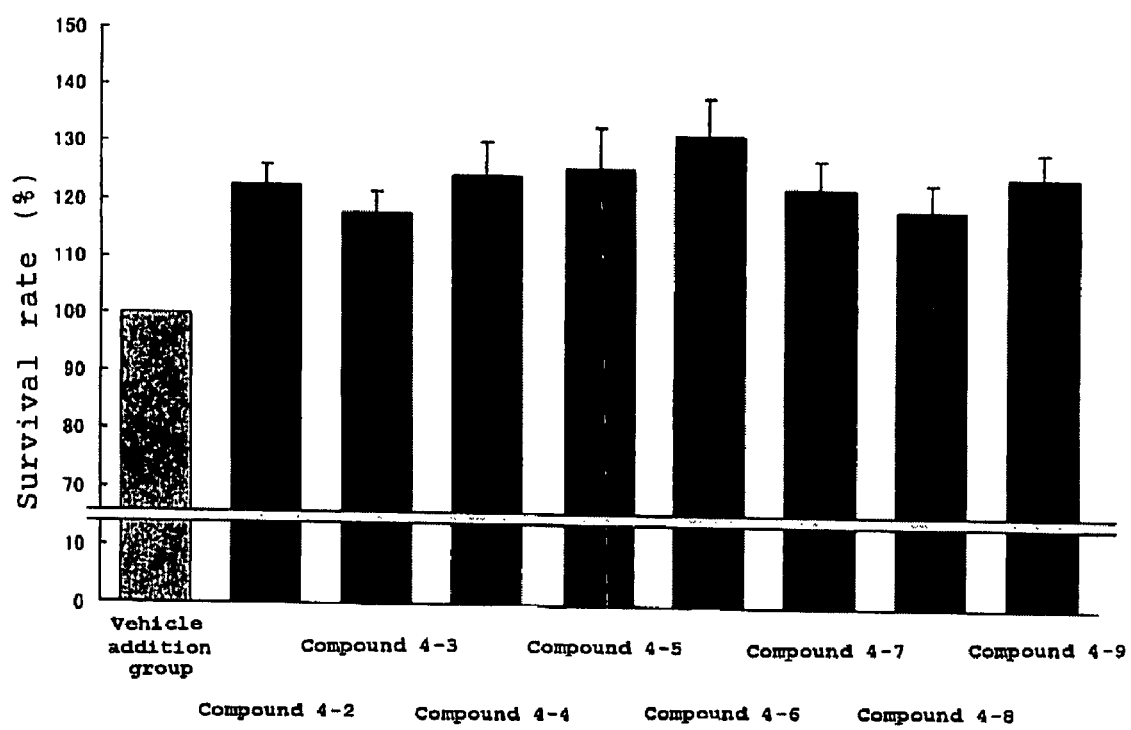

PROTECTIVE AGENT FOR RETINAL NEURONAL CELL COMPRISING INDAZOLE DERIVATIVE AS ACTIVE INGREDIENT

This application is the United States national phase application of International Application PCT/JP2006/307715 filed Apr. 12, 2006.

TECHNICAL FIELD

The present invention relates to a protective agent for a retinal neuronal cell comprising an indazole derivative as an active ingredient.

BACKGROUND ART

The retina is a tissue with a thickness of from 0.1 to 0.5 mm which is composed of ten layers of inner limiting membrane, nerve fiber layer, ganglion cell layer, inner plexiform layer, inner nuclear layer, outer plexiform layer, outer nuclear layer, outer limiting membrane, photoreceptor cell layer and retinal pigment epithelium layer, and retinal neuronal cell groups including photoreceptor cells, bipolar cells, ganglion cells, horizontal cells, amacrine cells and Muller cells are present therein.

The retinal neuronal cells play an important role in the reception and transmission of visual information such as converting light stimulation into an electrical signal and transmitting the signal to the brain.

To specifically describe the mechanism of such transmission, the visual information from the eyes is converted into an electrical signal through photoreceptor cells and transmitted to ganglion cells by way of horizontal cells, bipolar cells and/or amacrine cells. Then, the electrical signal is transmitted to the brain by way of the optic nerve which is a bundle of optic nerve fibers including axons of ganglion cells.

When these retinal neuronal cells are damaged due to various causes, the homeostasis (a function to supply oxygen or nutrition to retinal neuronal cells through retinal blood circulation and the like) of retinal neuronal cells cannot be maintained, and the transmission of visual information to the brain is inhibited. For example, it is widely known that dysfunction of retinal neuronal cells is caused in various retinal diseases such as retinal vascular occlusion, diabetic retinopathy, ischemic optic neuropathy, glaucoma, macular degeneration, retinitis pigmentosa and Leber's disease (Brain Res. Bull., 62(6), 447-453 (2004)).

It has recently been considered that retinal neuronal cell death due to retinal ischemia is one of the causes of retinal neuronal cell damage, and the following events and the like have been reported regarding the retinal neuronal cell death due to retinal ischemia (JP-A-2003-146904 and Nature Rev., 2, 448-459 (2003)).

1) The mechanism of retinal neuronal cell death due to retinal ischemia is similar to that of cerebral neuronal cell death during cerebral ischemia.
2) In short term retinal ischemia, the retinal inner layer (inner plexiform layer) is selectively damaged.
3) The excess release of glutamate during retinal ischemia can be observed.
4) By the injection of an excitatory amino acid such as glutamate into the vitreous body, retinal neuronal cell death is induced.
5) The overstimulation mediated by retinal N-methyl-D-aspartate (NMDA) receptors promotes calcium (Ca) influx into cells, which results in inducing cell damage by way of induction of nitrogen monoxide (NO).

From these, it is considered that a drug such as a glutamate neurotoxicity inhibitor, a NMDA receptor antagonist or a NO synthesis inhibitor is useful for the treatment of an eye disease caused by retinal neuronal cell damage, and various studies have been carried out.

For example, JP-A-2001-072591 discloses a protective agent for a retinal neuronal cell comprising nipradilol which is one of the β-blockers as an active ingredient. WO 01/056606 discloses a protective agent for an optic ganglion cell comprising an interleukin-1 receptor antagonist protein as an active ingredient. WO 03/004058 discloses a protective agent for an optic ganglion cell comprising an $\alpha_1$ receptor antagonist such as bunazosin hydrochloride as an active ingredient. Experimental Eye Res., 72, 479-486 (2001) discloses an effect of protecting a neuronal cell of latanoprost which is one of the prostaglandin derivatives, etc.

On the other hand, WO 2005/035506 discloses an indazole derivative as a Rho kinase inhibitor.

However, this publication does not disclose an effect of protecting a retinal neuronal cell of an indazole derivative at all.

DISCLOSURE OF THE INVENTION

Problems to be Solved

It is a very interesting subject to find a new medicinal use of an indazole derivative.

Means of Solving Problems

Accordingly, the present inventors made intensive studies for the purpose of finding a new medicinal use of an indazole derivative. As a result, they found that the indazole derivative inhibits glutamate-induced retinal neuronal cell death in rat fetal retinal neuronal cells, in other words, the indazole derivative acts directly on the retinal neuronal cells and exhibits an effect of protecting retinal neuronal cells, and thus the present invention has been accomplished.

The "indazole derivative" as used herein means a compound represented by the following general formula (1) or a salt thereof, and the present invention is directed to a protective agent for a retinal neuronal cell comprising the compound or a salt thereof as an active ingredient.

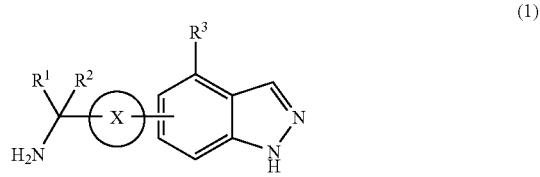

(1)

[The ring X represents a benzene ring or a pyridine ring;
$R^1$ and $R^2$ are the same or different and represent a hydrogen atom or an alkyl group;
$R^1$ and $R^2$ may be joined together to form a cycloalkane ring;
$R^3$ represents a hydroxy group, an alkoxy group, an aryloxy group, a cycloalkyl group, an alkylamino group, an arylamino group, a nitro group, a cyano group or a monocyclic heterocycle; and
a cyclic moiety of the benzene ring, pyridine ring, cycloalkane ring, aryloxy group, cycloalkyl group, arylamino group or monocyclic heterocycle defined above may have one or plural substituents selected from a halogen atom, an alkoxy group and an alkyl group, and an alkyl moiety of the alkyl group, alkoxy group or alkylamino group defined above may have one or plural substituents selected from a halogen atom and an alkoxy group. Hereinafter the same shall apply.]

The respective rings, atoms and groups defined in this specification will be described in detail below.

The "cycloalkane ring" refers to a cycloalkane ring having 3 to 8 carbon atoms. Specific examples thereof include cyclopropane, cyclobutane, cyclopentane, cyclohexane, cycloheptane, cyclooctane, and the like.

The "monocyclic heterocycle" refers to a saturated or unsaturated monocyclic heterocycle which has one or plural heteroatoms selected from a nitrogen atom, an oxygen atom and a sulfur atom in the ring, and has 2 to 6 carbon atoms.

Specific examples of the "saturated monocyclic heterocycle" include pyrrolidine, pyrazolidine, imidazolidine, triazolidine, piperidine, hexahydropyridazine, hexahydropyrimidine, piperazine, homopiperidine, homopiperazine and the like, each of which has a nitrogen atom in the ring; tetrahydrofuran, tetrahydropyran and the like, each of which has an oxygen atom in the ring; tetrahydrothiophene, tetrahydrothiopyran and the like, each of which has a sulfur atom in the ring; oxazolidine, isoxazolidine, morpholine and the like, each of which has a nitrogen atom and an oxygen atom in the ring; thiazolidine, isothiazolidine, thiomorpholine and the like, each of which has a nitrogen atom and a sulfur atom in the ring, and the like.

Specific examples of the "unsaturated monocyclic heterocycle" include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, pyrazine and the like, each of which has a nitrogen atom in the ring; dihydrofuran, furan, dihydropyran, pyran and the like, each of which has an oxygen atom in the ring; dihydrothiophene, thiophene, dihydrothiopyran, thiopyran and the like, each of which has a sulfur atom in the ring; dihydrooxazole, oxazole, dihydroisoxazole, isoxazole, dihydrooxazine, oxazine and the like, each of which has a nitrogen atom and an oxygen atom in the ring; dihydrothiazole, thiazole, dihydroisothiazole, isothiazole, dihydrothiazine, thiazine and the like, each of which has a nitrogen atom and a sulfur atom in the ring, and the like.

The "halogen atom" refers to fluorine, chlorine, bromine or iodine.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "alkoxy" refers to straight-chain or branched alkoxy having 1 to 6 carbon atoms. Specific examples thereof include methoxy, ethoxy, n-propoxy, n-butoxy, n-pentoxy, n-hexyloxy, isopropoxy, isobutoxy, sec-butoxy, tert-butoxy, isopentoxy and the like.

The "aryloxy" refers to monocyclic aromatic hydrocarbonoxy, or bicyclic or tricyclic condensed polycyclic aromatic hydrocarbonoxy having 6 to 14 carbon atoms. Specific examples thereof include phenoxy, naphthyloxy, anthryloxy, phenanthryloxy and the like.

The "cycloalkyl" refers to cycloalkyl having 3 to 8 carbon atoms. Specific examples thereof include cyclopropyl, cyclobutyl, cyclopentyl, cyclohexyl, cycloheptyl, cyclooctyl and the like.

The "alkylamino" refers to monoalkylamino or dialkylamino having 1 to 12 carbon atoms. Specific examples thereof include methylamino, ethylamino, ethylmethylamino, dimethylamino, diethylamino, dihexylamino and the like.

The "arylamino" refers to monoarylamino or diarylamino having 6 to 28 carbon atoms. Specific examples thereof include phenylamino, naphthylamino, methylphenylamino, ethylphenylamino diphenylamino and the like.

In the case where the "indazole derivative" has a "free hydroxy group", a "free amino group", a "free alkylamino group", a "free arylamino group", or a "monocyclic heterocycle having a free nitrogen atom" as a substituent, these groups may be protected with a protecting group.

The protecting group for the "free hydroxy group" refers to a group commonly used as a protecting group for the "free hydroxy group" including a substituted or unsubstituted alkyl group, or an unsubstituted alkenyl group such as a methoxymethyl group, a benzyl group, a trityl group, a 4-methoxyphenylmethyl group, a benzyloxymethyl group, a methyl group or an allyl group; a substituted or unsubstituted heterocyclic group such as a 3-bromotetrahydropyranyl group, a tetrahydropyranyl group or a tetrahydrofuranyl group; a substituted or unsubstituted alkylcarbonyl group or a substituted or unsubstituted arylcarbonyl group such as a trifluoroacetyl group, an acetyl group, a 4-chlorobenzoyl group or a benzoyl group; a substituted or unsubstituted alkyloxycarbonyl group, an unsubstituted alkenyloxycarbonyl group, or a substituted or unsubstituted aryloxycarbonyl group such as a benzyloxycarbonyl group, a 4-methoxybenzyloxycarbonyl group, a 9-fluorenylmethoxycarbonyl group, a methoxycarbonyl group, an ethoxycarbonyl group, an isobutoxycarbonyl group, a tert-butoxycarbonyl group, a vinyloxycarbonyl group, an allyloxycarbonyl group, a 4-nitrophenyloxycarbonyl group or a phenyloxycarbonyl group; a substituted silyl group such as a trimethylsilyl group, a triethylsilyl group, a triisopropylsilyl group, a tert-butyldimethylsilyl group, a tert-butyldiphenylsilyl group; and the like.

The protecting group for the "free amino group", "free alkylamino group", "free arylamino group", or "monocyclic heterocycle having a free nitrogen atom" refers to a group commonly used as a protecting group for the "free amino group", "free alkylamino group", "free arylamino group", or "monocyclic heterocycle having a free nitrogen atom" including a substituted alkyl group or an unsubstituted alkenyl group such as a benzyl group, a trityl group, a diphenylmethyl group, a (4-methoxyphenyl) diphenylmethyl group or an allyl group; a hydrocarbonyl group such as a formyl group; a substituted or unsubstituted alkylcarbonyl group, a substituted or unsubstituted arylcarbonyl group, or an unsubstituted heterocyclic carbonyl group such as a trichloroacetyl group, a trifluoroacetyl group, an acetyl group, a 4-chlorobenzoyl group, a benzoyl group or a picolinoyl group; a substituted or unsubstituted alkyloxycarbonyl group, or a substituted or unsubstituted aryloxycarbonyl group such as a 2,2,2-trichloroethoxycarbonyl group, a benzyloxycarbonyl group, a diphenylmethoxycarbonyl group, a methoxycarbonyl group, an isobutoxycarbonyl group, a tert-butoxycarbonyl group, 3-nitrophenoxycarbonyl group or a phenoxycarbonyl group; a substituted or unsubstituted alkylsulfonyl group, or a substituted or unsubstituted arylsulfonyl group such as a benzylsulfonyl group, a tolylsulfonyl group, a methylsulfonyl group, a 4-chlorophenylsulfonyl group, 2,4,6-trimethylphenyl sulfonyl group or a phenylsulfonyl group; and the like.

Further, the "nitrogen atom of the indazole ring" of the "indazole derivative" may be protected with a protecting group.

The protecting group for the nitrogen atom of the indazole ring refers to a group commonly used as a protecting group for the "nitrogen atom of the indazole ring" including a substituted alkyl group or an unsubstituted alkenyl group such as a benzyl group, a trityl group, a diphenylmethyl group, a (4-methoxyphenyl) diphenylmethyl group or an allyl group; a hydrocarbonyl group such as a formyl group; a substituted or unsubstituted alkylcarbonyl group, a substituted or unsubstituted arylcarbonyl group, or an unsubstituted heterocyclic carbonyl group such as a trichloroacetyl group, a trifluoroacetyl group, an acetyl group, a 4-chlorobenzoyl group, a benzoyl group or a picolinoyl group; a substituted or unsubstituted alkyloxycarbonyl group, or a substituted or unsubstituted aryloxycarbonyl group such as a 2,2,2-trichloroethoxycarbonyl group, a benzyloxycarbonyl group, a diphenylmethoxycarbonyl group, a methoxycarbonyl group, an isobutoxycarbonyl group, a tert-butoxycarbonyl group, a phenoxycarbonyl group or 3-nitrophenoxycarbonyl group; a substituted or unsubstituted alkylsulfonyl group, or a substituted or unsubstituted arylsulfonyl group such as a benzylsulfonyl group, a tolylsulfonyl group, a methylsulfonyl group, a 4-chlorophenylsulfonyl group, 2,4,6-trimethylphenyl sulfonyl group or a phenylsulfonyl group; a substituted or unsubstituted heterocyclic group such as a 3-bromotetrahydropyranyl group, a tetrahydropyranyl group or a tetrahydrofuranyl group; and the like.

With regard to the "plural groups" in the present invention, the respective groups may be the same or different from one another. Further, in the "group" as used herein, respective atoms and rings are also included. The "plural" as used herein refers to the maximum number that can be substituted in the group or ring with substitution, and preferably refers to 2 or 3.

The "salt" in the present invention is not particularly limited as long as it is a pharmaceutically acceptable salt. Specific examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, lactic acid, methanesulfonic acid, trifluoromethanesulfonic acid or p-toluenesulfonic acid; salts with an alkali metal such as lithium, sodium or potassium; salts with an alkaline earth metal such as calcium or magnesium; quaternary salts with ammonia, methyl iodide or the like, and these salts are also included in the present invention.

In the case where there are geometrical isomers or optical isomers in the "indazole derivative", these isomers are also included in the scope of the present invention.

The "indazole derivative" may be in the form of a hydrate or a solvate.

Further, in the case where there is proton tautomerism in the "indazole derivative", the tautomeric isomers thereof are also included in the scope of the present invention.

(a) Preferred examples of the "indazole derivative" of the present invention include compounds in which the respective groups are groups described below in the compounds represented by the general formula (1) and salts thereof:
(a1) the ring X represents a benzene ring or a pyridine ring; and/or
(a2) $R^1$ and $R^2$ are the same or different and represent an alkyl group; and/or
(a3) $R^3$ represents an alkoxy group, a cycloalkyl group, an alkylamino group, a nitro group, a cyano group or a monocyclic heterocycle; and/or
(a4) an alkyl moiety of the alkoxy group defined in the above (a3) may be substituted with one or plural halogen atoms.

That is, preferred examples thereof include in the compounds represented by the general formula (1), compounds that satisfy one or a combination of two or more selected from the above (a1), (a2), (a3) and (a4), and salts thereof.

(b) More preferred examples of the "indazole derivative" of the present invention include compounds in which the respective groups are groups shown below in the compounds represented by the general formula (1) and salts thereof:
(b1) the ring X represents a benzene ring or a pyridine ring; and/or
(b2) $R^1$ and $R^2$ represent a methyl group; and/or
(b3) $R^3$ represents a methoxy group, a difluoromethoxy group, a cyclopropyl group, a dimethylamino group, a nitro group, a cyano group, a pyrrolidine ring or an isoxazole ring.

That is, more preferred examples thereof include in the compounds represented by the general formula (1), compounds that satisfy one or a combination of two or more selected from the above (b1), (b2) and (b3), and salts thereof.

(c) Further, in the compounds represented by the general formula (1), an "indazole derivative" which satisfies the requirement of the above (a) or (b), and in which the ring X is positioned at the 5-position of the indazole ring is furthermore preferred.

(d) Further, in the compounds represented by the general formula (1), an "indazole derivative" which satisfies the requirement of the above (c), and in which in the case where the position where the ring X is bonded to the indazole ring is taken as the 1-position, a substituent represented by the following general formula (2) is substituted at the 4-position of the ring X is particularly preferred.

(2)

(e) Particularly preferred specific examples of the "indazole derivative" of the present invention include the following compounds and salts thereof.

5-[4-(1-amino-1-methylethyl)phenyl]-4-nitro-1H-indazole
5-[4-(1-amino-1-methylethyl)phenyl]-4-dimethylamino-1H-indazole
5-[4-(1-amino-1-methylethyl)phenyl]-4-(pyrrolidin-1-yl)-1H-indazole
5-[4-(1-amino-1-methylethyl)phenyl]-4-methoxy-1H-indazole
5-[4-(1-amino-1-methylethyl)phenyl]-4-cyano-1H-indazole
5-[5-(1-amino-1-methylethyl)pyridin-2-yl]-4-difluoromethoxy-1H-indazole
5-[4-(1-amino-1-methylethyl)phenyl]-4-(isoxazol-5-yl)-1H-indazole
5-[5-(1-amino-1-methylethyl)pyridin-2-yl]-4-cyclopropyl-1H-indazole The "retinal neuronal cell" in the present invention means a neuronal cell involved in the transmission of visual signal to the brain. Specifically, it means a photoreceptor cell, a horizontal cell, a bipolar cell, an optic ganglion cell, an amacrine cell or the like.

The "eye disease" in the present invention means an eye disease associated with retinal neuronal cell damage or retinal damage. Specifically, it means abnormal visual field, retinal vascular occlusion, diabetic retinopathy, ischemic optic neuropathy, glaucoma, macular degeneration, retinitis pigmentosa, Leber's disease or the like, and preferably it means abnormal visual field, retinal vascular occlusion, diabetic retinopathy, ischemic optic neuropathy, macular degeneration, retinitis pigmentosa or Leber's disease. The present invention is useful for the prevention or treatment of such a disease.

The "indazole derivative" in the present invention can be produced by the method described in International Publication No. WO 2005/035506 (International Application No. PCT/JP2004/015663).

Further, a representative method for producing the "indazole derivative" in the present invention will be shown below. Incidentally, specific method for producing each of the "indazole derivatives" will be described in detail in the "section of Production Examples" in the Examples which will be mentioned later.

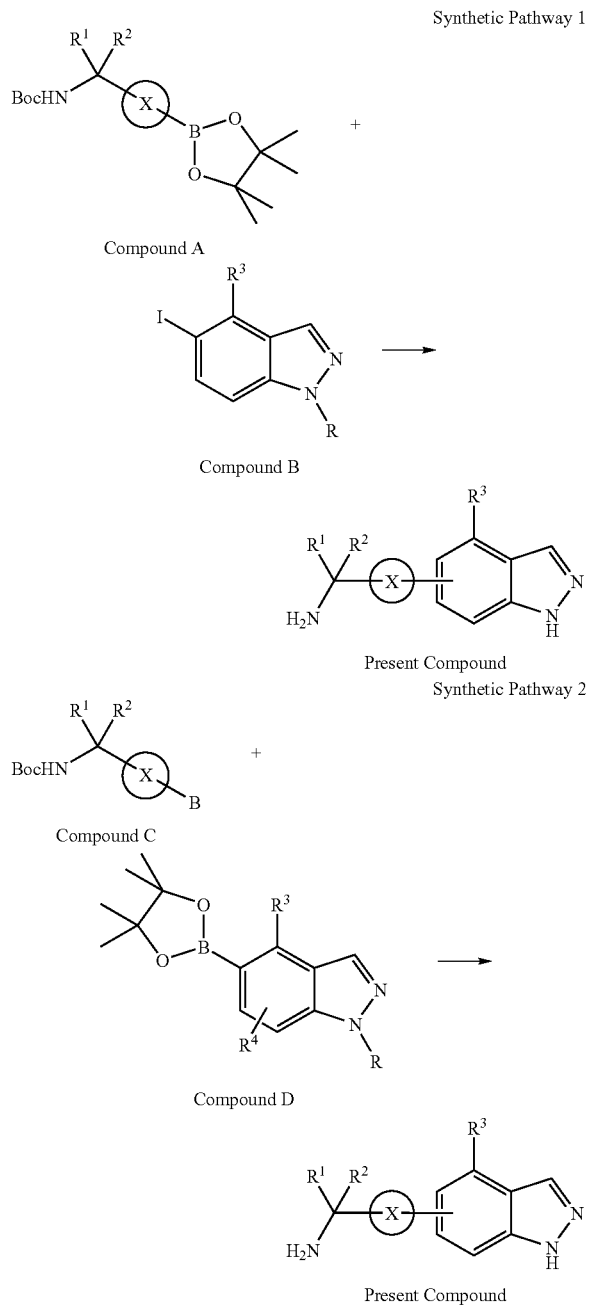

Synthetic pathway 1 or synthetic pathway 2: The compound A is subjected to a coupling reaction with the compound B, or the compound C is subjected to a coupling reaction with the compound D, in an organic solvent in the presence of a metal catalyst and/or a base, whereby the "indazole derivative" can be obtained.

In the case where a protective group is used for the convenience of the production in the above-mentioned production method, the protective group can be removed by a widely used method.

With regard to the substituent on the ring X and/or the indazole ring, a desired substituent may be introduced in its initial stage or it is also acceptable that, after the fundamental skeleton is produced by the above-mentioned method, the desired substituent may be introduced into the fundamental skeleton using oxidation, reduction, alkylation, esterification, amidation, oximation, dehydration reaction, deprotection reaction, acetylation, hydrolysis, triflation, coupling reaction, cyclization reaction and/or a commonly used synthetic method in which the above-mentioned reactions are combined.

A method for producing a synthetic intermediate of the "indazole derivative" will be described in detail in the "section of Production Examples" in the Examples which will be mentioned later.

The "indazole derivative" of the present invention can be administered either orally or parenterally. Examples of the dosage form for administration include tablets, capsules, granules, powders, injection, eye drops and the like, and they can be prepared by widely used techniques in combination.

For example, an oral preparation such as a tablet, a capsule, a granule or a powder can be prepared by combining an indazole derivative together, if necessary, with an excipient such as lactose, mannitol, starch, crystalline cellulose, light anhydrous silicic acid, calcium carbonate or calcium hydrogen phosphate, a lubricant such as stearic acid, magnesium stearate or talc, a binder such as starch, hydroxypropyl cellulose, hydroxypropylmethyl cellulose and polyvinylpyrrolidone, a disintegrant such as carboxymethyl cellulose, low-substituted hydroxypropylmethyl cellulose or calcium citrate, a coating agent such as hydroxypropylmethyl cellulose, macrogol or a silicone resin, a stabilizer such as ethyl p-hydroxybenzoate or benzyl alcohol, a corrigent such as a sweetener, a sour agent or a flavor, or the like.

A parenteral preparation such as an injection or an eye drop can be prepared by combining an indazole derivative together, if necessary, with a tonicity agent such as glycerin, propylene glycol, sodium chloride, potassium chloride, sorbitol or mannitol, a buffer such as phosphoric acid, phosphate, citric acid, glacial acetic acid, ε-aminocaproic acid or trometamol; a pH adjusting agent such as hydrochloric acid, citric acid, phosphoric acid, glacial acetic acid, sodium hydroxide, potassium hydroxide, sodium carbonate or sodium hydrogen carbonate, a solubilizer or dispersant such as polysorbate 80, polyoxyethylene hydrogenated castor oil 60, macrogol 4000, purified soybean lecithin or polyoxyethylene (160) polyoxypropylene (30) glycol, a cellulosic polymer such as hydroxypropylmethyl cellulose or hydroxypropyl cellulose, a viscous agent such as polyvinyl alcohol or polyvinylpyrrolidone, a stabilizer such as edetic acid or sodium edetate, a commonly used preservative or antiseptic such as sorbic acid, potassium sorbate, benzalkonium chloride, benzethonium chloride, methyl p-hydroxybenzoate, propyl p-hydroxybenzoate or chlorobutanol, a soothing agent such as chlorobutanol, benzyl alcohol or lidocaine, or the like.

In the case of an injection or an eye drop, it is desired that the pH is adjusted to 4.0 to 8.0 and that the osmotic pressure ratio is adjusted to about 1.0.

The present invention also relates to a method of protecting a retinal neuronal cell comprising administering an effective amount of the above-mentioned compound or a salt thereof to a patient, a method of preventing or treating a disease associated with retinal neuronal cell damage comprising administering an effective amount of the above-mentioned compound or a salt thereof to a patient, and a method of preventing or treating retinal neuronal cell damage comprising administering an effective amount of the above-mentioned compound or a salt thereof to a patient.

The dose of the "indazole derivative" can be appropriately selected for use depending on the symptoms, age, dosage form and the like. For example, in the case of an oral preparation, usually 0.01 to 1000 mg per day, preferably 1 to 100 mg per day can be administered once or divided into several times a day.

Further, in the case of an eye drop, usually an eye drop containing the indazole derivative at a concentration of from 0.0001% to 10% (w/v), preferably from 0.01% to 5% (w/v) can be administered once or divided into several times a day.

ADVANTAGE OF THE INVENTION

As will be described in detail in the section of Pharmacological Tests mentioned below, an effect of an indazole derivative on glutamate-induced retinal neuronal cell death was examined using rat fetal retinal neuronal cells. As a result, the indazole derivative acted directly on the retinal neuronal cells and inhibited the glutamate-induced retinal neuronal cell death.

That is, the indazole derivative has an effect of protecting a retinal neuronal cell, and is useful for the prevention or treatment of an eye disease associated with retinal neuronal cell damage or retinal damage.

BEST MODE FOR CARRYING OUT THE INVENTION

Hereinafter, Production Examples of the "indazole derivatives" (Examples 1 to 15) according to the present invention and synthetic intermediates thereof (Reference Examples 1 to 27), Preparation Examples and results of Pharmacological Tests will be described. However, these examples are described for the purpose of understanding the present invention better and are not meant to limit the scope of the present invention. Further, the Rf values in the physical properties of Examples are represented by the values measured using a thin-layer chromatography (manufactured by Merck Ltd., TLC plate silica gel $60F_{254}$ (trade name)), and in the chemical structural formulae, Me represents a methyl group, Bn represents a benzyl group, Ac represents an acetyl group, Boc represents a tert-butoxycarbonyl group, Tf represents a trifluoromethanesulfonyl group, TBS represents a tert-butyldimethylsilyl group, and THP represents a tetrahydropyranyl group unless otherwise specified.

PRODUCTION EXAMPLES

Reference Example 1

Synthesis of 1-bromo-4-(1-cyano-1-methylethyl) benzene (Reference Compound 1-1)

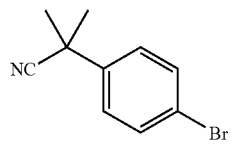

45 g (1100 mmol) of sodium hydride (a 60% dispersion in a mineral oil) was added in divided portions to a solution of 100 g (510 mmol) of 4-bromophenylacetonitrile in 1500 ml of N,N-dimethylformamide at 0° C. in an argon stream with stirring. Then, 95 ml (1500 mmol) of methyl iodide was added dropwise thereto at 0° C. with stirring and the mixture was stirred at 10° C. for 1 hour.

After the reaction was completed, the reaction solution was gradually poured into 900 g of a saturated aqueous solution of ammonium chloride, then 500 ml of water was added thereto and the mixture was extracted with 2000 ml of ethyl acetate. The organic layer was washed with a saturated aqueous solution of sodium chloride, dried over anhydrous sodium sulfate and concentrated under reduced pressure, whereby 110 g of the title compound was obtained as a dark brown oily substance (yield: 96%).

Rf value: 0.78 (n-hexane:ethyl acetate=1:1 (v/v))
Mass spectrum (CI, m/z): 224, 226 ($M^+$+1)
$^1$H-NMR spectrum (CDCl$_3$, δppm): 1.71 (s, 6H), 7.32-7.38 (m, 2H), 7.49-7.54 (m, 2H)

Hereinafter, Reference compound 1-2 was produced in accordance with the production method for the Reference compound 1-1.

2-Bromo-5-(1-cyano-1-methylethyl)pyridine (Reference Compound 1-2)

Rf value: 0.32 (n-hexane:ethyl acetate=4:1 (v/v))
Mass spectrum (CI, m/z): 225, 227 ($M^+$+1)
IR spectrum (KBr, cm$^{-1}$): 2243
$^1$H-NMR spectrum (CDCl$_3$, δppm): 1.76 (s, 6H), 7.52 (d, J=8.3 Hz, 1H), 7.67 (dd, J1=8.3 Hz, J2=2.7 Hz, 1H), 8.50 (d, J=2.7 Hz, 1H)

Reference Example 2

Synthesis of 4-(1-aminocarbonyl-1-methylethyl)-1-bromobenzene (Reference Compound 2)

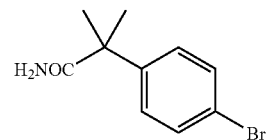

250 g (1800 mmol) of potassium trimethylsilanolate (purity: 90%) was added to a solution of 100 g (450 mmol) of 1-bromo-4-(1-cyano-1-methylethyl)benzene (Reference compound 1-1) in 1000 ml of toluene at room temperature in an argon stream with stirring and the mixture was stirred for 4.5 hours under a condition of heating to reflux.

After the reaction was completed, the reaction solution was cooled down to room temperature and 500 ml of water was added dropwise thereto. The mixed solution was stirred for 25 minutes at room temperature and the resulting solid was obtained by filtration and washed with 400 ml of water, whereby 99 g of the title compound was obtained as white powder (yield: 92%).

Melting point: 139 to 141° C.
Rf value: 0.23 (n-hexane:ethyl acetate=1:1 (v/v))
Mass spectrum (CI, m/z): 242, 244 ($M^+$+1)
$^1$H-NMR spectrum (CDCl$_3$, δppm): 1.56 (s, 6H), 5.18 (brs, 1H) 5.52 (brs, 1H), 7.25-7.30 (m, 2H), 7.46-7.51 (m, 2H)

Reference Example 3

Synthesis of 5-(1-aminocarbonyl-1-methylethyl)-2-bromopyridine (Reference Compound 3)

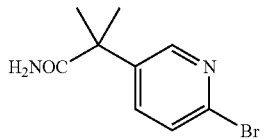

9.60 ml (93.3 mmol) of a 35% aqueous solution of hydrogen peroxide and 1.86 g (13.5 mmol) of potassium carbonate were added to a solution of 1.50 g (6.66 mmol) of 2-bromo-5-(1-cyano-1-methylethyl)pyridine (Reference compound 1-2) in 15 ml of dimethyl sulfoxide at 0° C. and the mixture was stirred for 15 minutes. Then, a cooling bath was removed and the mixture was stirred on a water bath for 2 hours.

After the reaction was completed, the reaction solution was poured into 200 ml of water and the mixture was extracted with 500 ml of 1,2-dichloroethane. The organic layer was successively washed with water and a saturated aqueous solution of sodium chloride, dried over anhydrous magnesium sulfate and concentrated under reduced pressure, whereby 1.63 g of the title compound was obtained as white powder (yield: quantitative).

Rf value: 0.17 (n-hexane:ethyl acetate=1:1 (v/v))
Mass spectrum (CI, m/z): 243, 245 (M$^+$+1)
$^1$H-NMR spectrum (CDCl$_3$, δppm): 1.61 (s, 6H), 5.36 (brs, 2H), 7.47 (dd, J1=8.3 Hz, J2=0.7 Hz, 1H), 7.59 (dd, J1=8.3 Hz, J2=2.7 Hz, 1H), 8.42 (dd, J1=2.7 Hz, J2=0.7 Hz, 1H)

Reference Example 4

Synthesis of 1-bromo-4-(1-tert-butoxycarbonylamino-1-methylethyl)benzene (Reference Compound 4-1)

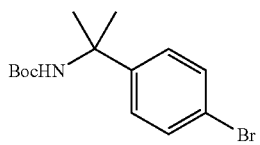

260 g (600 mmol) of [bis(trifluoroacetoxy)iodo]benzene was added to a solution of 99 g (410 mmol) of 4-(1-aminocarbonyl-1-methylethyl)-1-bromobenzene (Reference Compound 2) in 1000 ml of tert-butanol at room temperature in an argon stream with stirring, and the mixture was stirred for 30 minutes under a condition of heating to reflux. Then, 100 ml (1200 mmol) of pyridine was added thereto and the mixture was stirred for 1 hour under a condition of heating to reflux.

After the reaction was completed, the reaction solution was concentrated under reduced pressure, and 500 g of an aqueous solution of 10% by weight of citric acid was added to the resulting residue, and then the mixture was extracted with 2000 ml of toluene. The organic layer was successively washed with a saturated aqueous solution of sodium hydrogen carbonate and a saturated aqueous solution of sodium chloride, dried over anhydrous sodium sulfate and concentrated under reduced pressure. 200 ml of n-hexane was added to the resulting residue and the resulting solid was collected by filtration and washed with 400 ml of cold n-hexane, whereby 77 g of the title compound was obtained as light brown powder (yield: 60%).

Melting point: 92 to 93° C.
Rf value: 0.56 (n-hexane:ethyl acetate=4:1 (v/v))
Mass spectrum (EI, m/z): 313, 315 (M$^+$)
$^1$H-NMR spectrum (CDCl$_3$, δppm): 1.36 (brs, 9H), 1.59 (s, 6H), 4.90 (brs, 1H), 7.24-7.29 (m, 2H), 7.39-7.45 (m, 2H)

Hereinafter, Reference compound 4-2 was produced in accordance with the production method for the Reference compound 4-1.

2-Bromo-5-(1-tert-butoxycarbonylamino-1-methylethyl)pyridine (Reference Compound 4-2)

Melting point: 100 to 103° C.
Rf value: 0.53 (n-hexane:ethyl acetate=2:1 (v/v))
Mass spectrum (CI, m/z): 315, 317 (M$^+$+1)
$^1$H-NMR spectrum (CDCl$_3$, δppm): 1.37 (brs, 9H), 1.61 (s, 6H), 4.95 (brs, 1H), 7.41 (dd, J1=8.3 Hz, J2=0.7 Hz, 1H), 7.56 (dd, J1=8.3 Hz, J2=2.7 Hz, 1H), 8.40 (dd, J1=2.7 Hz, J2=0.7 Hz, 1H)

Reference Example 5

Synthesis of 4-(1-tert-butoxycarbonylamino-1-methylethyl)-1-(4,4,5,5-tetramethyl[1,3,2]dioxaborolanyl)benzene (Reference Compound 5)

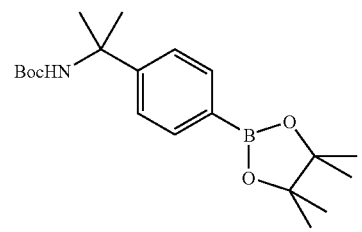

370 ml (350 mmol) of a 0.95 M sec-butyl lithium/n-hexane solution was added dropwise to a solution of 50 g (160 mmol) of 1-bromo-4-(1-tert-butoxycarbonylamino-1-methylethyl)benzene (Reference Compound 4-1) in 800 ml of diethyl ether at −78° C. in an argon stream with stirring, and the mixture was stirred for 30 minutes. Then, 97 ml (480 mmol) of 2-isopropoxy-4,4,5,5-tetramethyl[1,3,2]dioxaborolane was added dropwise thereto at −78° C. and the mixture was stirred at −50° C. for 2 hours.

After the reaction was completed, 300 g of a saturated aqueous solution of ammonium chloride was added to the resulting solution, and 450 ml of water was poured into the solution to separate the mixture into layers. An aqueous layer was extracted with 300 ml of ethyl acetate again and the organic layers were combined, washed with a saturated aqueous solution of sodium chloride, dried over anhydrous sodium sulfate and concentrated under reduced pressure. 100 ml of n-hexane was added to the resulting residue and the resulting solid was collected by filtration and successively washed with 100 ml of a mixed solvent (n-hexane:ethyl acetate=4:1 (v/v)) and 100 ml of n-hexane, whereby 33 g of the title compound was obtained as white powder (yield: 58%).

Melting point: 142 to 144° C.
Rf value: 0.38 (n-hexane:ethyl acetate=4:1 (v/v))
Mass spectrum (CI, m/z): 362 (M$^+$+1)
$^1$H-NMR spectrum (CDCl$_3$, δppm): 1.10-1.50 (m, 21H), 1.61 (s, 6H), 4.93 (brs, 1H), 7.37-7.42 (m, 2H), 7.74-7.79 (m, 2H)

Reference Example 6

Synthesis of 5-iodo-1H-indazole (Reference Compound 6)

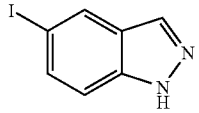

95 ml (570 mmol) of 6 N hydrochloric acid was added dropwise to a solution of 25.0 g (188 mmol) of 5-amino-1H-indazole in 320 ml of N,N-dimethylformamide at 0° C. and the mixture was stirred for 20 minutes. Then, a solution of 13.6 g (197 mmol) of sodium nitrite in 75 ml of water was added dropwise thereto while keeping the temperature of the reaction solution at not higher than 10° C. After the mixture was stirred for 30 minutes, 32.8 g (198 mmol) of potassium iodide was added thereto in divided portions, then a cooling bath was removed to warm up the mixture gradually to room temperature.

After the reaction was completed, the reaction solution was poured into 1000 ml of water and the mixture was neutralized with an aqueous solution of sodium hydroxide and extracted with 1500 ml of toluene and then with each 500 ml of toluene twice. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure. 50 ml of ethyl acetate was added to the resulting crude crystals, the mixture was heated to dissolve them, 300 ml of n-hexane was added thereto and the resulting solid was collected by filtration, whereby 5.80 g of the title compound was obtained as white powder (yield: 13%).

Rf value: 0.45 (n-hexane:ethyl acetate=1:1 (v/v))
Mass spectrum (CI, m/z): 245 (M$^+$+1)
$^1$H-NMR spectrum (CDCl$_3$, δppm): 7.30 (ddd, J1=8.8 Hz, J2=1.1 Hz, J3=0.7 Hz, 1H), 7.63 (dd, J1=8.8 Hz, J2=1.5 Hz, 1H), 8.01 (d, J=1.1 Hz, 1H), 8.14 (dd, J1=1.5 Hz, J2=0.7 Hz, 1H), 10.17 (brs, 1H)

Reference Example 7

Synthesis of 1-acetyl-5-iodo-1H-indazole (Reference Compound 7)

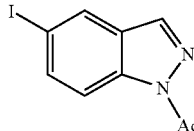

10 ml of acetic acid and 20 ml of acetic anhydride were added to 1.02 g (4.18 mmol) of 5-iodo-1H-indazole (Reference compound 6) and the mixture was stirred at room temperature for 30 minutes.

After the reaction was completed, the reaction solution was poured into 300 ml of water and the resulting solid was collected by filtration, whereby 1.08 g of the title compound was obtained as white powder (yield: 90%).

Rf value: 0.49 (n-hexane:ethyl acetate=4:1 (v/v))
Mass spectrum (CI, m/z): 287 (M$^+$+1)
$^1$H-NMR spectrum (CDCl$_3$, δppm): 2.78 (s, 3H), 7.81 (dd, J1=8.8 Hz, J2=1.6 Hz, 1H), 8.05 (d, J=0.9 Hz, 1H), 8.10 (dd, J1=1.6 Hz, J2=0.7 Hz, 1H), 8.23 (ddd, J1=8.8 Hz, J2=0.9 Hz, J3=0.7 Hz, 1H)

Reference Example 8

Synthesis of 5-iodo-4-nitro-1H-indazole (Reference Compound 8)

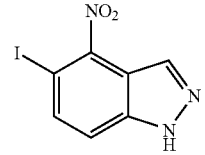

12.5 ml of nitric acid was gradually added dropwise to a solution of 1.57 g (6.43 mmol) of 5-iodo-1H-indazole (Reference compound 6) in 25 ml of concentrated sulfuric acid at 0° C. and the mixture was stirred for 1 hour. Then, a cooling bath was removed to warm up the mixture gradually to room temperature.

After the reaction was completed, the reaction solution was gradually poured into 150 ml of ice water, and the mixture was neutralized with an aqueous solution of sodium hydroxide and extracted with each 300 ml of ethyl acetate for three times. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=3:1 (v/v)) and the fraction containing the desired substance was concentrated under reduced pressure, whereby 0.90 g of the title compound was obtained as yellow powder (yield: 48%).

Rf value: 0.32 (n-hexane:ethyl acetate=1:1 (v/v))
Mass spectrum (CI, m/z): 290 (M$^+$+1)
$^1$H-NMR spectrum (CDCl$_3$, δppm): 7.69 (dd, J1=8.8 Hz, J2=1.0 Hz, 1H), 7.98 (d, J=8.8 Hz, 1H), 8.23 (d, J=1.0 Hz, 1H), 13.88 (brs, 1H)

Reference Example 9

Synthesis of 1-tert-butoxycarbonyl-5-iodo-4-nitro-1H-indazole (Reference Compound 9-1)

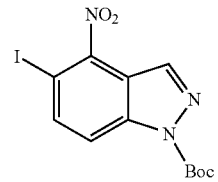

38.0 mg (0.31 mmol) of 4-dimethylaminopyridine and 18 ml of tetrahydrofuran were added to 898 mg (3.11 mmol) of 5-iodo-4-nitro-1H-indazole (Reference compound 8). Then, a solution of 1.36 g (6.23 mmol) of di-tert-butyl dicarbonate in 9 ml of tetrahydrofuran was added thereto in an argon stream with stirring and the mixture was stirred at room temperature for 1 hour.

After the reaction was completed, the reaction solution was concentrated under reduced pressure, the resulting residue was subjected to silica gel column chromatography (eluting solvent: n-hexane:ethyl acetate=20:1 (v/v)) and the fraction containing the desired substance was concentrated under reduced pressure, whereby 1.17 g of the title compound was obtained as yellow powder (yield: 97%).

Rf value: 0.33 (n-hexane:ethyl acetate=4:1 (v/v))
Mass spectrum (CI, m/z): 390 (M$^+$+1)
$^1$H-NMR spectrum (CDCl$_3$, δppm): 1.73 (s, 9H), 8.11 (d, J=8.8 Hz, 1H), 8.19 (dd, J1=8.8 Hz, J2=0.7 Hz, 1H), 8.40 (d, J=0.7 Hz, 1H)

Hereinafter, Reference compounds 9-2 and 9-3 were produced in accordance with the production method for the Reference compound 9-1.

1-tert-Butoxycarbonyl-5-iodo-3-methoxycarbonyl-1H-indazole (Reference Compound 9-2)

Rf value: 0.51 (n-hexane:ethyl acetate=2:1 (v/v))
Mass spectrum (CI, m/z): 403 (M$^+$+1)
$^1$H-NMR spectrum (CDCl$_3$, δppm): 1.73 (s, 9H), 4.05 (s, 3H), 7.32 (dd, J1=8.9 Hz, J2=1.7 Hz, 1H), 7.99 (dd, J1=8.9 Hz, J2=0.7 Hz, 1H), 8.64 (dd, J1=1.7 Hz, J2=0.7 Hz, 1H)

1-tert-Butoxycarbonyl-3-formyl-5-iodo-1H-indazole (Reference Compound 9-3)

Rf value: 0.54 (n-hexane:ethyl acetate=4:1 (v/v))
Mass spectrum (CI, m/z): 373 (M$^+$+1)
$^1$H-NMR spectrum (CDCl$_3$, δppm): 1.76 (s, 9H), 7.85 (dd, J1=9.0 Hz, J2=1.7 Hz, 1H), 7.96 (dd, J1=9.0 Hz, J2=0.7 Hz, 1H), 8.71 (dd, J1=1.7 Hz, J2=0.7 Hz, 1H), 10.30 (s, 1H)

Reference Example 10

Synthesis of 5-iodo-3-methoxycarbonyl-1H-indazole (Reference Compound 10)

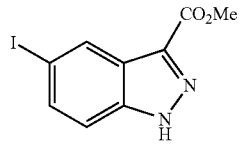

A solution of 2.72 g (68.0 mmol) of sodium hydroxide in 120 ml of water was added to 17.5 g (64.1 mmol) of 5-iodoisatin and the mixture was stirred at room temperature for 15 minutes. Then, a solution of 4.96 g (71.9 mmol) of sodium nitrite in 20 ml of water was added thereto at 0° C. and a solution of 12.2 g (124 mmol) of concentrated sulfuric acid in 120 ml of water was added dropwise thereto while keeping the temperature of the reaction solution at not higher than 10° C. After the mixture was stirred for 30 minutes, a solution of 30.8 g (162 mmol) of anhydrous tin (II) chloride in 60 ml of concentrated hydrochloric acid was added dropwise thereto while keeping the temperature of the reaction solution at not higher than 10° C. After the dropwise addition was completed, a cooling bath was removed to warm up the mixture gradually to room temperature and the mixture was stirred for 2 hours.

Thereafter, the resulting solid was collected by filtration, 300 ml of methanol and 1 ml of concentrated sulfuric acid were added to 22.9 g of the resulting crude crystals and the mixture was stirred for 10 hours under a condition of heating to reflux.

After the reaction was completed, the reaction solution was filtered and the filtrate was concentrated under reduced pressure and poured into 500 ml of water. The mixed solution was neutralized with an aqueous solution of sodium hydroxide and extracted with 1000 ml of chloroform. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure. 50 ml of ethyl acetate was added to the resulting crude crystals, the mixture was heated to dissolve the crystals, 300 ml of n-hexane was added thereto and the resulting solid was collected by filtration, whereby 4.93 g of the title compound was obtained as brown powder (yield: 26%).

Rf value: 0.44 (n-hexane:ethyl acetate=1:1 (v/v))
Mass spectrum (CI, m/z): 303 (M$^+$+1)
$^1$H-NMR spectrum (CDCl$_3$, δppm): 4.06 (s, 3H), 7.38 (dd, J1=8.8 Hz, J2=0.6 Hz, 1H), 7.72 (dd, J1=8.8 Hz, J2=1.5 Hz, 1H), 8.64 (dd, J1=1.5 Hz, J2=0.6 Hz, 1H), 10.70 (brs, 1H)

Reference Example 11

Synthesis of 3-hydroxymethyl-5-iodo-1H-indazole (Reference Compound 11)

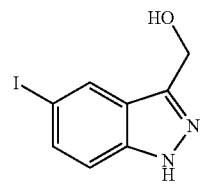

32 ml (32.0 mmol) of a 1 M solution of diisobutyl aluminum hydride in toluene was added dropwise to a solution of 2.41 g (7.89 mmol) of 5-iodo-3-methoxycarbonyl-1H-indazole (Reference compound 10) in 80 ml of tetrahydrofuran at −78° C. in an argon stream with stirring. The mixture was stirred at −78° C. for 30 minutes and then stirred at 0° C. for 2.5 hours.

After the reaction was completed, a saturated aqueous solution of ammonium chloride was gradually added to the reaction solution at 0° C., then 300 ml of ethyl acetate was added thereto and the mixture was filtered through Celite (trade name). The filtrate was dried over anhydrous magnesium sulfate and concentrated under reduced pressure, whereby 2.31 g of the title compound was obtained as yellow powder (yield: quantitative).

Rf value: 0.25 (n-hexane:ethyl acetate=1:1 (v/v))
Mass spectrum (CI, m/z): 275 (M$^+$+1)
$^1$H-NMR spectrum (DMSO-d$_6$, δppm): 4.75 (d, J=5.8 Hz, 2H), 5.26 (t, J=5.8 Hz, 1H), 7.35 (dd, J1=8.8 Hz, J2=0.7 Hz, 1H), 7.56 (dd, J1=8.8 Hz, J2=1.7 Hz, 1H), 8.25 (dd, J1=1.7 Hz, J2=0.7 Hz, 1H), 12.93 (brs, 1H)

Reference Example 12

Synthesis of 3-formyl-5-iodo-1H-indazole (Reference Compound 12)

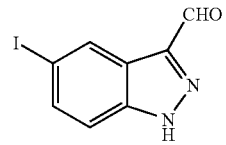

6.94 g (79.8 mmol) of manganese dioxide was added to a solution of 2.31 g (8.43 mmol) of 3-hydroxymethyl-5-iodo-1H-indazole (Reference compound 11) in 50 ml of tetrahydrofuran and 50 ml of dichloromethane and the mixture was stirred at room temperature for 1 hour.

After the reaction was completed, the reaction solution was filtered and the filtrate was concentrated under reduced pressure. The resulting residue was subjected to silica gel column chromatography (eluting solvent: n-hexane:ethyl acetate=1:1 (v/v)) and the fraction containing the desired substance was concentrated under reduced pressure, whereby 1.84 g of the title compound was obtained as brown powder (yield: 80%).

Rf value: 0.57 (n-hexane:ethyl acetate=1:1 (v/v))
Mass spectrum (CI, m/z): 273 (M$^+$+1)
$^1$H-NMR spectrum (DMSO-d$_6$, δppm): 7.58 (dd, J1=8.8 Hz, J2=0.7 Hz, 1H), 7.76 (dd, J1=8.8 Hz, J2=1.7 Hz, 1H), 8.49 (dd, J1=1.7 Hz, J2=0.7 Hz, 1H), 10.17 (s, 1H), 14.30 (brs, 1H)

Reference Example 13

Synthesis of 2-benzyloxy-6-nitrotoluene (Reference Compound 13)

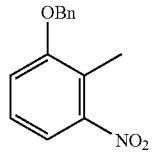

41.5 g (300 mmol) of potassium carbonate and 200 ml of N,N-dimethylformamide were added to 30.6 g (200 mmol) of 2-methyl-3-nitrophenol. Then, 23.8 ml (200 mmol) of benzyl bromide was added thereto in an argon stream with stirring and the mixture was stirred at room temperature for 3 hours.

After the reaction was completed, the reaction solution was poured into 1000 ml of water and the mixture was extracted with 800 ml of toluene and 500 ml of the same twice. The organic layer was successively washed with water and a saturated aqueous solution of sodium chloride, dried over anhydrous magnesium sulfate and concentrated under reduced pressure, whereby 49.3 g of the title compound was obtained as yellow powder (yield: quantitative).

Rf value: 0.48 (n-hexane:ethyl acetate=4:1 (v/v))
Mass spectrum (CI, m/z): 244 (M$^+$+1)
$^1$H-NMR spectrum (CDCl$_3$, δppm): 2.42 (s, 3H), 5.13 (s, 2H), 7.08-7.11 (m, 1H), 7.21-7.27 (m, 1H), 7.32-7.44 (m, 6H)

Reference Example 14

Synthesis of 3-benzyloxy-2-methylaniline (Reference Compound 14)

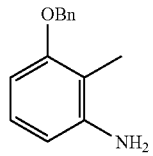

52.3 g (800 mmol) of zinc was added in divided portions at 0° C. to a solution of 49.3 g (203 mmol) of 2-benzyloxy-6-nitrotoluene (Reference compound 13) in 400 ml of methanol and 200 ml of acetic acid in an argon stream with stirring and the mixture was stirred for 1 hour.

After the reaction was completed, the reaction solution was poured into 1600 ml of water and the mixture was extracted with 1500 ml of ethyl acetate. The organic layer was successively washed with water, a saturated aqueous solution of sodium hydrogen carbonate and a saturated aqueous solution of sodium chloride, dried over anhydrous magnesium sulfate and concentrated under reduced pressure, whereby 44.0 g of the title compound was obtained as a brown oily substance (yield: quantitative).

Rf value: 0.22 (n-hexane:ethyl acetate=4:1 (v/v))
Mass spectrum (EI, m/z): 213 (M$^+$)
$^1$H-NMR spectrum (CDCl$_3$, δppm): 2.11 (s, 3H), 3.64 (brs, 2H), 5.05 (s, 2H), 6.36-6.39 (m, 1H), 6.41 (d, J=8.3 Hz, 1H), 6.93-6.99 (m, 1H), 7.29-7.46 (m, 5H)

Reference Example 15

Synthesis of 3-benzyloxy-2-methylacetanilide (Reference Compound 15-1)

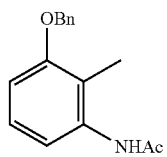

28.3 ml (299 mmol) of acetic anhydride was added to a solution of 44.0 g (206 mmol) of 3-benzyloxy-2-methylaniline (Reference compound 14) in 400 ml of ethyl acetate and the mixture was stirred for 30 minutes under a condition of heating to reflux.

After the reaction was completed, the reaction solution was poured into 2000 ml of hexane and the resulting solid was collected by filtration and washed with hexane, whereby 44.9 g of the title compound was obtained as white powder (yield: 85%).

Rf value: 0.24 (n-hexane:ethyl acetate=1:1 (v/v))
Mass spectrum (CI, m/z): 256 (M$^+$+1)
$^1$H-NMR spectrum (DMSO-d$_6$, δppm): 2.04 (s, 3H), 2.06 (s, 3H), 5.11 (s, 2H), 6.87 (d, J=7.9 Hz, 1H), 6.96-7.00 (m, 1H), 7.09 (dd, J1=7.9 Hz, J2=7.9 Hz, 1H), 7.29-7.48 (m, 5H), 9.31 (brs, 1H)

Hereinafter, Reference compound 15-2 was produced in accordance with the production method for the Reference compound 15-1.

3-Methoxy-2-methylacetanilide (Reference Compound 15-2)

Rf value: 0.20 (n-hexane:ethyl acetate=1:1 (v/v))
Mass spectrum (CI, m/z): 180 (M$^+$+1)
$^1$H-NMR spectrum (DMSO-d$_6$, δppm): 2.00 (s, 3H), 2.03 (s, 3H), 3.78 (s, 3H), 6.78 (d, J=8.0 Hz, 1H), 6.93-6.97 (m, 1H), 7.07-7.13 (m, 1H), 9.29 (brs, 1H)

Reference Example 16

Synthesis of 1-acetyl-4-benzyloxy-1H-indazole (Reference Compound 16-1)

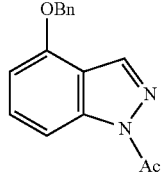

1.61 g (4.99 mmol) of tetra-n-butylammonium bromide, 19.6 g (200 mmol) of potassium acetate and 450 ml of ethyl acetate were added to 25.5 g (100 mmol) of 3-benzyloxy-2-methylacetanilide (Reference compound 15-1). Then, 28.4 ml (300 mmol) of acetic anhydride and 26.8 ml (200 mmol) of isoamyl nitrite were added thereto in an argon stream with stirring and the mixture was stirred for 9 hours under a condition of heating to reflux.

After the reaction was completed, the reaction solution was poured into 500 ml of water to separate into layers. The organic layer was successively washed with a saturated aqueous solution of sodium hydrogen carbonate and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=50:1 to 20:1 (v/v)) and the fraction containing the desired substance was concentrated under reduced pressure, whereby 17.7 g of the title compound was obtained as yellow powder (yield: 66%).

Rf value: 0.41 (n-hexane:ethyl acetate=4:1 (v/v))
Mass spectrum (CI, m/z): 267 ($M^+$+1)
$^1$H-NMR spectrum (CDCl$_3$, δppm): 2.78 (s, 3H), 5.24 (s, 2H), 6.78 (d, J=7.9 Hz, 1H), 7.34-7.50 (m, 6H), 8.00-8.03 (m, 1H), 8.24 (d, J=1.0 Hz, 1H)

Hereinafter, Reference compound 16-2 was produced in accordance with the production method for the Reference compound 16-1.

1-Acetyl-4-methoxy-1H-indazole (Reference Compound 16-2)

Rf value: 0.53 (n-hexane:ethyl acetate=2:1 (v/v))
Mass spectrum (CI, m/z): 191 ($M^+$+1)
$^1$H-NMR spectrum (CDCl$_3$, δppm): 2.78 (s, 3H), 3.98 (s, 3H), 6.71 (d, J=8.1 Hz, 1H), 7.46 (dd, J1=8.3 Hz, J2=8.1 Hz, 1H), 7.98-8.01 (m, 1H), 8.20 (d, J=0.7 Hz, 1H)

Reference Example 17

Synthesis of 4-benzyloxy-5-bromo-1H-indazole (Reference Compound 17-1)

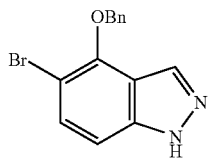

13.0 g (73.0 mmol) of N-bromosuccinimide was added to a solution of 17.7 g (66.5 mmol) of 1-acetyl-4-benzyloxy-1H-indazole (Reference compound 16-1) in 330 ml of tetrahydrofuran at 0° C. in an argon stream with stirring and the mixture was stirred for 30 minutes and then stirred at room temperature for 15 hours.

Thereafter, 300 ml of methanol and 130 ml of a 1 N aqueous solution of sodium hydroxide were added to the reaction solution and the mixture was stirred at room temperature for 30 minutes.

After the reaction was completed, the reaction solution was neutralized with a 1 N aqueous solution of hydrochloric acid and concentrated under reduced pressure. The resulting residue was extracted with 500 ml of ethyl acetate and the organic layer was successively washed with a saturated aqueous solution of sodium hydrogen carbonate and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=6:1 to 4:1 (v/v)) and the fraction containing the desired substance was concentrated under reduced pressure, whereby 13.6 g of the title compound was obtained as light orange powder (yield: 67%).

Rf value: 0.25 (n-hexane:ethyl acetate=2:1 (v/v))
Mass spectrum (EI, m/z): 302, 304 ($M^+$)
$^1$H-NMR spectrum (CDCl$_3$, δppm): 5.40 (s, 2H), 7.10 (dd, J1=8.8 Hz, J2=1.0 Hz, 1H), 7.33-7.44 (m, 3H), 7.49-7.55 (m, 3H), 8.06 (d, J=1.0 Hz, 1H), 10.14 (brs, 1H)

Hereinafter, Reference compound 17-2 was produced in accordance with the production method for the Reference compound 17-1.

5-Bromo-4-methoxy-1H-indazole (Reference Compound 17-2)

Rf value: 0.17 (n-hexane:ethyl acetate=2:1 (v/v))
Mass spectrum (EI, m/z): 226, 228 ($M^+$)
$^1$H-NMR spectrum (CDCl$_3$, δppm): 4.25 (s, 3H), 7.06 (dd, J1=8.7 Hz, J2=1.0 Hz, 1H), 7.49 (d, J=8.7 Hz, 1H), 8.23 (d, J=1.0 Hz, 1H), 10.09 (brs, 1H)

Reference Example 18

Synthesis of 4-benzyloxy-5-bromo-2-(tetrahydropyran-2-yl)-2H-indazole (Reference Compound 18-1)

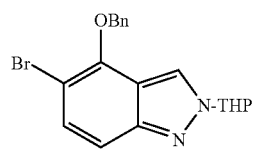

3.39 g (13.5 mmol) of pyridinium p-toluenesulfonate and 450 ml of methylene chloride were added to 13.6 g (44.9 mmol) of 4-benzyloxy-5-bromo-1H-indazole (Reference compound 17-1). Then, 12.3 ml (135 mmol) of 3,4-dihydro-2H-pyran was added thereto at 0° C. in an argon stream with stirring and the mixture was stirred for 30 minutes. Then, the mixture was stirred at room temperature for 3 hours.

After the reaction was completed, the reaction solution was poured into 300 ml of a saturated aqueous solution of sodium hydrogen carbonate to separate into layers. The organic layer was successively washed with a 10% aqueous solution of citric acid, water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=6:1 (v/v)) and a high polar fraction (Rf value: 0.36 (n-hexane:ethyl acetate=2:1 (v/v)) was concentrated under reduced pressure, whereby 15.5 g of the title compound was obtained as an orange oily substance (yield: 89%).

Rf value: 0.36 (n-hexane:ethyl acetate=2:1 (v/v))
Mass spectrum (EI, m/z): 386, 388 ($M^+$)
$^1$H-NMR spectrum (CDCl$_3$, δppm): 1.66-1.80 (m, 3H), 2.02-2.23 (m, 3H), 3.73-3.81 (m, 1H), 4.09-4.14 (m, 1H), 5.27 (s, 2H), 5.60-5.64 (m, 1H), 7.32-7.43 (m, 5H), 7.51-7.54 (m, 2H), 8.07 (s, 1H)

Hereinafter, Reference compounds 18-2 to 18-4 were produced in accordance with the production method for the Reference compound 18-1.

5-tert-Butyldimethylsilyloxy-4-formyl-2-(tetrahydropyran-2-yl)-2H-indazole (Reference Compound 18-2)

Rf value: 0.63 (n-hexane:ethyl acetate=1:1 (v/v))

Mass spectrum (CI, m/z): 361 (M⁺+1)

¹H-NMR spectrum (CDCl₃, δppm): 0.30 (s, 6H), 1.05 (s, 9H), 1.50-2.30 (m, 6H), 3.70-3.85 (m, 1H), 4.05-4.20 (m, 1H), 5.70-5.80 (m, 1H), 6.99 (d, J=9.3 Hz, 1H), 7.93 (d, J=9.3 Hz, 1H), 8.82 (s, 1H), 10.54 (s, 1H)

5-(tert-Butyldimethylsilyloxy)-4-methylcarbonyl-2-(tetrahydropyran-2-yl)-2H-indazole (Reference Compound 18-3)

Property: white powder

Rf value: 0.37 (n-hexane:ethyl acetate=2:1 (v/v))

Mass spectrum (CI, m/z): 375 (M⁺+1)

¹H-NMR spectrum (CDCl₃, δppm): 0.32 (s, 6H), 1.02 (s, 9H), 1.62-1.82 (m, 3H), 2.00-2.13 (m, 1H), 2.15-2.30 (m, 2H), 2.69 (s, 3H), 3.73-3.82 (m, 1H), 4.06-4.15 (m, 1H), 5.65-5.73 (m, 1H), 6.99 (d, J=9.4 Hz, 1H), 7.82 (d, J=9.4 Hz, 1H), 8.67 (s, 1H)

5-Bromo-4-methoxy-2-(tetrahydropyran-2-yl)-2H-indazole (Reference Compound 18-4)

Rf value: 0.27 (n-hexane:ethyl acetate=2:1 (v/v))

Mass spectrum (EI, m/z): 310, 312 (M⁺)

¹H-NMR spectrum (CDCl₃, δppm): 1.68-1.81 (m, 3H), 2.04-2.29 (m, 3H), 3.75-3.83 (m, 1H), 4.08-4.36 (m, 4H), 5.63-5.68 (m, 1H), 7.31 (dd, J1=9.0 Hz, J2=1.0 Hz, 1H), 7.36 (d, J=9.0 Hz, 1H), 8.28 (d, J=1.0 Hz, 1H)

Reference Example 19

Synthesis of 4-benzyloxy-5-bromo-1-(tetrahydropyran-2-yl)-1H-indazole (Reference Compound 19)

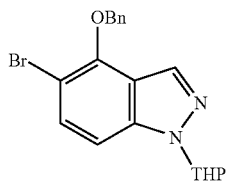

In the synthesis for Reference compound 18-1, a low polar fraction (Rf value: 0.52 (n-hexane:ethyl acetate=2:1 (v/v)) was concentrated under reduced pressure, whereby 1.18 g of the title compound was obtained as a yellow oily substance (yield: 7%).

Rf value: 0.52 (n-hexane:ethyl acetate=2:1 (v/v))

Mass spectrum (EI, m/z): 386, 388 (M⁺)

¹H-NMR spectrum (CDCl₃, δppm): 1.66-1.79 (m, 3H), 2.04-2.15 (m, 2H), 2.49-2.55 (m, 1H), 3.69-3.78 (m, 1H), 3.98-4.04 (m, 1H), 5.36 (s, 2H), 5.64-5.68 (m, 1H), 7.20 (dd, J1=8.9 Hz, J2=0.9 Hz, 1H), 7.31-7.43 (m, 3H), 7.49-7.60 (m, 3H), 7.99 (d, J=0.9 Hz, 1H)

Reference Example 20

Synthesis of 1-acetyl-5-(4,4,5,5-tetramethyl[1,3,2]dioxaborolanyl)-1H-indazole (Reference Compound 20-1)

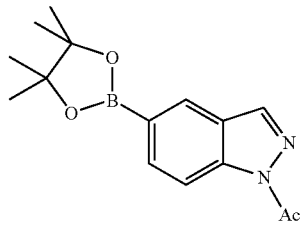

270 mg (0.38 mmol) of dichlorobis (triphenylphosphine) palladium and 18 ml of 1,4-dioxane were added to 1.1 g (3.8 mmol) of 1-acetyl-5-iodo-1H-indazole (Reference compound 7). Then, 1.7 ml (12 mmol) of 4,4,5,5-tetramethyl[1,3,2]dioxaborolane and 1.6 ml (12 mmol) of triethylamine were added thereto in an argon stream with stirring and the mixture was stirred at 80° C. for 1 hour.

After the reaction was completed, the reaction solution was poured into 50 ml of water and the mixture was extracted with 200 ml of ethyl acetate. The organic layer was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=10:1 (v/v)) and the fraction containing the desired substance was concentrated under reduced pressure, whereby 0.70 g of the title compound was obtained as yellow powder (yield: 64%).

Rf value: 0.41 (n-hexane:ethyl acetate=4:1 (v/v))

Mass spectrum (CI, m/z): 287 (M⁺+1)

¹H-NMR spectrum (CDCl₃, δppm): 1.37 (s, 12H), 2.79 (s, 3H) 7.98 (dd, J1=8.3 Hz, J2=1.0 Hz, 1H), 8.12 (d, J=0.7 Hz, 1H), 8.22-8.24 (m, 1H), 8.42 (ddd, J1=8.3 Hz, J2=1.0 Hz, J3=0.7 Hz, 1H)

Hereinafter, Reference compound 20-2 was produced in accordance with the production method for the Reference compound 20-1.

4-Benzyloxy-1-(tetrahydropyran-2-yl)-5-(4,4,5,5-tetramethyl[1,3,2]dioxaborolanyl)-1H-indazole (Reference Compound 20-2)

Rf value: 0.31 (n-hexane:ethyl acetate=4:1 (v/v))

Mass spectrum (CI, m/z): 435 (M⁺+1)

¹H-NMR spectrum (CDCl₃, δppm): 1.36 (s, 12H), 1.65-1.79 (m, 3H), 2.02-2.18 (m, 2H), 2.49-2.63 (m, 1H), 3.70-3.79 (m, 1H), 4.01-4.07 (m, 1H), 5.37 (s, 2H), 5.66-5.71 (m, 1H), 7.24 (dd, J1=8.4 Hz, J2=0.7 Hz, 1H), 7.29-7.41 (m, 3H), 7.57-7.62 (m, 2H), 7.72 (d, J=8.4 Hz, 1H), 8.09 (d, J=0.7 Hz, 1H)

Reference Example 21

Synthesis of 5-hydroxy-4-methylcarbonyl-1H-indazole (Reference Compound 21)

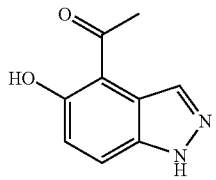

30 g (220 mmol) of aluminum chloride was added to a solution of 10 g (67 mmol) of 5-methoxy-1H-indazole (see R. A. Bartsch, et al., J. Heterocyclic Chem., vol. 21, p. 1063 (1984)) in 200 ml of 1,2-dichloroethane at room temperature in an argon stream and the mixture was stirred for 30 minutes. Then, 12 ml (170 mmol) of acetyl chloride was added thereto at room temperature and the mixture was stirred at 60° C. for 2.5 hours.

After the reaction was completed, the reaction solution was allowed to cool, water was added thereto and the mixture was extracted with chloroform. The organic layer was successively washed with a saturated aqueous solution of sodium hydrogen carbonate and a saturated aqueous solution of sodium chloride, dried over anhydrous magnesium sulfate and concentrated under reduced pressure. The resulting residue was washed with chloroform, whereby 3.6 g of the title compound was obtained as yellow powder (yield: 30%).

Melting point: 188 to 191° C.
Rf value: 0.14 (n-hexane:ethyl acetate=2:1 (v/v))
Mass spectrum (CI, m/z): 177 (M$^+$+1)
$^1$H-NMR spectrum (DMSO-d$_6$, δppm): 2.79 (s, 3H), 7.05 (d, J=8.9 Hz, 1H), 7.81 (dd, J1=8.9 Hz, J2=0.9 Hz, 1H), 8.25 (d, J=0.9 Hz, 1H), 12.61 (brs, 1H), 13.38 (brs, 1H)

Reference Example 22

Synthesis of 4-formyl-5-methoxy-1H-indazole (Reference Compound 22)

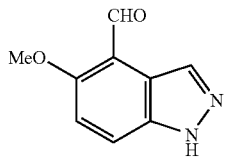

45.0 g (337 mmol) of aluminum chloride was added to a solution of 25.0 g (169 mmol) of 5-methoxy-1H-indazole in 500 ml of methylene chloride in an argon stream and the mixture was stirred at room temperature for 30 minutes. The resulting mixture was cooled down to −10° C., 17.5 ml (193 mmol) of dichloromethyl methyl ether was added dropwise thereto over 20 minutes and the mixture was stirred at 0° C. for 2 hours.

After the reaction was completed, 300 ml of a mixed solution of methanol:water=1:1 (v/v) was gradually poured into the reaction solution at 0° C. and the resulting solid was collected by filtration and washed with chloroform. Then, 300 ml of chloroform, 150 ml of methanol and 150 ml of a saturated aqueous solution of sodium hydrogen carbonate were added to the resulting solid and the mixture was stirred at room temperature for 1 hour. The resulting mixed solution was extracted with 150 ml of a mixed solvent of chloroform:methanol=2:1 (v/v) and the organic layer was dried over anhydrous magnesium sulfate and concentrated under reduced pressure. Chloroform was added to the resulting solid, the mixture was subjected to an ultrasonic treatment. The solid was collected by filtration and washed with chloroform, whereby 7.20 g of the title compound was obtained as green powder (yield: 24%).

Rf value: 0.50 (ethyl acetate)
Mass spectrum (CI, m/z): 177 (M$^+$+1)
$^1$H-NMR spectrum (DMSO-d$_6$, δppm): 4.00 (s, 3H), 7.40 (d, J=9.0 Hz, 1H), 7.93 (dd, J1=9.0 Hz, J2=1.0 Hz, 1H), 8.43 (d, J=1.0 Hz, 1H), 10.57 (s, 1H), 13.32 (brs, 1H)

Reference Example 23

Synthesis of 4-formyl-5-hydroxy-1H-indazole monohydrobromide (Reference Compound 23)

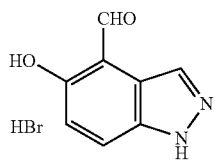

A solution of 25.0 g (100 mmol) of boron tribromide in 50 ml of methylene chloride was added to a solution of 10.1 g (57.3 mmol) of 4-formyl-5-methoxy-1H-indazole (Reference compound 22) in 50 ml of methylene chloride and the mixture was stirred at room temperature for 2 hours. Then, 50.0 ml of a 1.0 M solution of boron tribromide/methylene chloride was added thereto and the mixture was stirred at room temperature for 7 hours.

After the reaction was completed, the reaction solution was cooled down to 0° C. and methanol was gradually added thereto. The mixture was concentrated under reduced pressure, a mixed solvent of diethyl ether:methanol=9:1 (v/v) was added thereto and the resulting solid was collected by filtration, whereby 11.2 g of the title compound was obtained as light gray powder (yield: 81%).

Rf value: 0.35 (chloroform:methanol: 28% aqueous ammonia=10:1:0.1 (v/v/v))
Mass spectrum (CI, m/z): 163 (M$^+$+1)
$^1$H-NMR spectrum (DMSO-d$_6$, δppm): 7.09 (d, J=9.0 Hz, 1H), 7.78 (dd, J1=9.0 Hz, J2=1.0 Hz, 1H), 8.36 (d, J=1.0 Hz, 1H), 10.53 (s, 1H), 10.66 (brs, 2H)

Reference Example 24

Synthesis of 5-tert-butyldimethylsilyloxy-4-formyl-1H-indazole (Reference Compound 24-1)

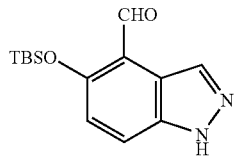

1.50 ml (8.61 mmol) of N,N-diisopropylethylamine and 700 mg (4.64 mmol) of tert-butyldimethylsilyl chloride were added at 0° C. to a solution of 955 mg (3.93 mmol) of 4-formyl-5-hydroxy-1H-indazole monohydrobromide (Reference compound 23) in 15 ml of tetrahydrofuran and the mixture was stirred at room temperature for 15 hours.

After the reaction was completed, water was added to the reaction solution and the mixture was extracted with ethyl acetate. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 to 1:1 (v/v)) and the fraction containing the desired substance was concentrated under reduced pressure, whereby 964 mg of the title compound was obtained as white solid (yield: 88%).

Rf value: 0.45 (n-hexane:ethyl acetate=1:1 (v/v))
Mass spectrum (CI, m/z): 277 ($M^+$+1)
$^1$H-NMR spectrum (CDCl$_3$, δppm): 0.31 (s, 6H), 1.06 (s, 9H) 7.11 (d, J=9.1 Hz, 1H), 7.82 (d, J=9.1 Hz, 1H), 8.59 (s, 1H), 10.63 (s, 1H)

Hereinafter, Reference compound 24-2 was produced in accordance with the production method for the Reference compound 24-1.

5-tert-Butyldimethylsilyloxy-4-methylcarbonyl-1H-indazole (Reference Compound 24-2)

Rf value: 0.28 (n-hexane:ethyl acetate=2:1 (v/v))
Mass spectrum (CI, m/z): 291 ($M^+$+1)
$^1$H-NMR spectrum (CDCl$_3$, δppm): 0.35 (s, 6H), 1.04 (s, 9H), 2.73 (s, 3H), 7.28 (d, J=9.4 Hz, 1H), 7.89 (dd, J1=9.4 Hz, J2=0.8 Hz, 1H), 8.83 (d, J=0.8 Hz, 1H)

Reference Example 25

Synthesis of 4-formyl-5-hydroxy-2-(tetrahydropyran-2-yl)-2H-indazole (Reference Compound 25-1)

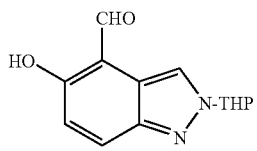

34.0 ml (34.0 mmol) of a 1.0 M solution of tetrabutylammonium fluoride/tetrahydrofuran was added to a solution of 10.1 g (28.0 mmol) of 5-tert-butyldimethylsilyloxy-4-formyl-2-(tetrahydropyran-2-yl)-2H-indazole (Reference compound 18-2) in 150 ml of tetrahydrofuran at 0° C. and the mixture was stirred at 0° C. for 1.5 hours.

After the reaction was completed, water was added to the reaction solution and the mixture was extracted with chloroform. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=6:1 to 3:2 (v/v)) and the fraction containing the desired substance was concentrated under reduced pressure, whereby 4.5 g of the title compound was obtained as a yellow foamy substance (yield: 65%)

Rf value: 0.10 (n-hexane:ethyl acetate=4:1 (v/v))
Mass spectrum (CI, m/z): 247 ($M^+$+1)
$^1$H-NMR spectrum (CDCl$_3$, δppm): 1.60-1.90 (m, 3H), 1.97-2.30 (m, 3H), 3.70-3.85 (m, 1H), 4.05-4.20 (m, 1H), 5.60-5.75 (m, 1H), 7.00 (d, J=9.3 Hz, 1H), 7.92 (dd, J1=9.3 Hz, J2=1.0 Hz, 1H), 8.31 (d, J=1.0 Hz, 1H), 10.25 (s, 1H), 12.10 (brs, 1H)

Hereinafter, Reference compound 25-2 was produced in accordance with the production method for the Reference compound 25-1.

5-Hydroxy-4-methylcarbonyl-2-(tetrahydropyran-2-yl)-2H-indazole (Reference Compound 25-2)

Property: yellow powder
Rf value: 0.28 (n-hexane:ethyl acetate=2:1 (v/v))
Mass spectrum (CI, m/z): 261 ($M^+$+1)
$^1$H-NMR spectrum (CDCl$_3$, δppm): 1.62-1.84 (m, 3H), 2.01-2.12 (m, 1H), 2.13-2.25 (m, 2H), 2.74 (s, 3H), 3.71-3.82 (m, 1H), 4.08-4.16 (m, 1H), 5.62-5.67 (m, 1H), 7.01 (d, J=9.4 Hz, 1H), 7.89 (dd, J1=9.4 Hz, J2=0.9 Hz, 1H), 8.07 (d, J=0.9 Hz, 1H), 14.09 (s, 1H)

Reference Example 26

Synthesis of 4-formyl-2-(tetrahydropyran-2-yl)-5-trifluoromethanesulfonyloxy-2H-indazole (Reference Compound 26-1)

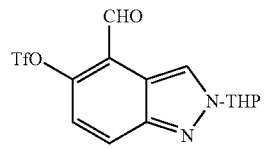

9.80 g (27.4 mmol) of N-phenylbis (trifluoromethanesulfonimide) and 15.0 ml (108 mmol) of triethylamine were added to a solution of 4.50 g (18.3 mmol) of 4-formyl-5-hydroxy-2-(tetrahydropyran-2-yl)-2H-indazole (Reference compound 25-1) in 100 ml of methylene chloride in an argon stream and the mixture was stirred at room temperature for 1 hour.

After the reaction was completed, water was added to the reaction solution and the mixture was extracted with chloroform. The organic layer was dried over anhydrous magnesium sulfate and concentrated under reduced pressure. The resulting residue was subjected to silica gel column chromatography (eluting solvent: n-hexane:ethyl acetate=6:1 to 4:1 (v/v)) and the fraction containing the desired substance was concentrated under reduced pressure, whereby 6.00 g of the title compound was obtained as white powder (yield: 87%).

Rf value: 0.30 (n-hexane:ethyl acetate=4:1 (v/v))
Mass spectrum (CI, m/z): 379 ($M^+$+1)
$^1$H-NMR spectrum (CDCl$_3$, δppm): 1.60-1.90 (m, 3H), 2.00-2.14 (m, 1H), 2.15-2.30 (m, 2H), 3.74-3.87 (m, 1H), 4.10-4.22 (m, 1H), 5.70-5.80 (m, 1H), 7.30 (d, J=9.3 Hz, 1H), 8.12 (dd, J1=9.3 Hz, J2=1.0 Hz, 1H), 8.96 (d, J=1.0 Hz, 1H), 10.49 (s, 1H)

Hereinafter, Reference compound 26-2 was produced in accordance with the production method for the Reference compound 26-1.

4-Methylcarbonyl-2-(tetrahydropyran-2-yl)-5-(trifluoromethanesulfonyloxy)-2H-indazole (Reference Compound 26-2)

Property: pale yellow oily substance
Rf value: 0.74 (n-hexane:ethyl acetate=1:1 (v/v))
Mass spectrum (CI, m/z): 393 ($M^+$+1)
$^1$H-NMR spectrum (CDCl$_3$, δppm): 1.65-1.87 (m, 3H), 1.97-2.29 (m, 3H), 2.76 (s, 3H), 3.74-3.85 (m, 1H), 4.10-4.18 (m, 1H), 5.67-5.73 (m, 1H), 7.26 (d, J=9.3 Hz, 1H), 7.96 (dd, J1=9.3 Hz, J2=1.0 Hz, 1H), 8.65 (d, J=1.0 Hz, 1H)

Reference Example 27

Synthesis of 3-amino-2-methylanisole (Reference Compound 27)

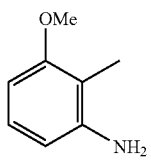

A suspension of 9.98 g of 5% palladium-carbon (hydrous) in 100 ml of ethanol was added to a solution of 30.7 g (184 mmol) of 2-methyl-3-nitroanisole in 300 ml of ethanol and the mixture was stirred for 3 hours at room temperature in a hydrogen atmosphere.

After the reaction was completed, the reaction solution was filtered through Celite and the filtrate was concentrated under reduced pressure, whereby 25.5 g of the title compound was obtained as a slightly purple oily substance (yield: quantitative).

Rf value: 0.38 (n-hexane:ethyl acetate=2:1 (v/v))
Mass spectrum (EI, m/z): 137 (M$^+$)
$^1$H-NMR spectrum (CDCl$_3$, δppm): 2.04-2.05 (m, 3H), 3.60 (brs, 2H), 3.80 (s, 3H), 6.33-6.37 (m, 2H), 6.94-7.01 (m, 1H) (Example 1)

Synthesis of 1-acetyl-5-[4-(1-tert-butoxycarbonylamino-1-methylethyl)phenyl]-1H-indazole (Compound 1-1)

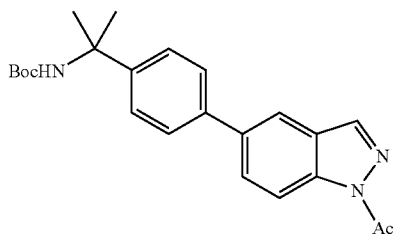

1.26 g (3.49 mmol) of 4-(1-tert-butoxycarbonylamino-1-methylethyl)-1-(4,4,5,5-tetramethyl[1,3,2]dioxaborolanyl)benzene (Reference compound 5), 792 mg (5.21 mmol) of cesium fluoride, 400 mg (0.346 mmol) of tetrakis(triphenylphosphine)palladium and 20 ml of 1,2-dimethoxyethane were added to 500 mg (1.74 mmol) of 1-acetyl-5-iodo-1H-indazole (Reference compound 7) and the mixture was stirred for 2 hours in an argon stream under a condition of heating to reflux.

After the reaction was completed, the reaction solution was poured into 50 ml of water and the mixture was extracted with 100 ml of ethyl acetate. The organic layer was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=5:1 (v/v)) and the fraction containing the desired substance was concentrated under reduced pressure, whereby 385 mg of the title compound was obtained as white powder (yield: 56%).

Rf value: 0.48 (n-hexane:ethyl acetate=2:1 (v/v))
Mass spectrum (CI, m/z): 394 (M$^+$+1)
$^1$H-NMR spectrum (CDCl$_3$, δppm): 1.40 (brs, 9H), 1.67 (s, 6H), 2.81 (s, 3H), 4.98 (brs, 1H), 7.48-7.52 (m, 2H), 7.57-7.61 (m, 2H), 7.80 (dd, J1=8.8 Hz, J2=1.7 Hz, 1H), 7.91 (dd, J1=1.7 Hz, J2=0.8 Hz, 1H), 8.17 (d, J=0.8 Hz, 1H), 8.46-8.50 (m, 1H)

Hereinafter, Compounds 1-2 to 1-9 were produced in accordance with the production method for the Compound 1-1. However, in the synthesis of Compound 1-4, an adduct of tris(dibenzylideneacetone)dipalladium with chloroform was used instead of tetrakis(triphenylphosphine) palladium and, in the synthesis of Compounds 1-5 to 1-9, a 2 M aqueous solution of sodium carbonate was used instead of cesium fluoride.

1-tert-Butoxycarbonyl-5-[4-(1-tert-butoxycarbonylamino-1-methylethyl)phenyl]-3-methoxycarbonyl-1H-indazole (Compound 1-2)

Rf value: 0.30 (n-hexane:ethyl acetate=2:1 (v/v))
$^1$H-NMR spectrum (CDCl$_3$, δppm): 1.40 (brs, 9H), 1.68 (s, 6H), (s, 9H), 4.06 (s, 3H), 4.97 (brs, 1H), 7.48-7.52 (m, 2H), 7.61-7.65 (m, 2H), 7.83 (dd, J1=8.8 Hz, J2=1.7 Hz, 1H), 8.24 (dd, J1=8.8 Hz, J2=0.7 Hz, 1H), 8.44 (dd, J1=1.7 Hz, J2=0.7 Hz, 1H)

1-tert-Butoxycarbonyl-5-[4-(1-tert-butoxycarbonylamino-1-methylethyl)phenyl]-3-formyl-1H-indazole (Compound 1-3)

Rf value: 0.48 (n-hexane:ethyl acetate=2:1 (v/v))

1-tert-Butoxycarbonyl-5-[4-(1-tert-butoxycarbonylamino-1-methylethyl)phenyl]-4-nitro-1H-indazole (Compound 1-4)

Rf value: 0.36 (n-hexane:ethyl acetate=2:1 (v/v))
Mass spectrum (FAB, m/z): 496 (M$^+$)
$^1$H-NMR spectrum (CDCl$_3$, δppm): 1.38 (brs, 9H), 1.67 (s, 6H), (s, 9H), 4.95 (brs, 1H), 7.31-7.34 (m, 2H), 7.46-7.51 (m, 2H), 7.60 (d, J=8.7 Hz, 1H), 8.42 (d, J=0.7 Hz, 1H), (dd, J1=8.7 Hz, J2=0.7 Hz, 1H)

4-Benzyloxy-5-[5-(1-tert-butoxycarbonylamino-1-methylethyl)pyridin-2-yl]-1-(tetrahydropyran-2-yl)-1H-indazole (Compound 1-5)

Rf value: 0.36 (n-hexane:ethyl acetate=1:1 (v/v))
Mass spectrum (CI, m/z): 543 (M$^+$+1)
$^1$H-NMR spectrum (CDCl$_3$, δppm): 1.38 (brs, 9H), 1.68-1.82 (m, 9H), 2.06-2.22 (m, 2H), 2.50-2.65 (m, 1H), 3.69-3.81 (m, 1H), 4.01-4.08 (m, 1H), 4.96 (brs, 1H), 5.31 (s, 2H), 5.69-5.74 (m, 1H), 7.26-7.33 (m, 5H), 7.38 (dd, J1=8.8 Hz, J2=0.9 Hz, 1H), 7.67 (dd, J1=8.4 Hz, J2=2.6 Hz, 1H), 7.85-7.91 (m, 2H), 8.09 (d, J=0.9 Hz, 1H), 8.75 (dd, J1=2.6 Hz, J2=0.9 Hz, 1H)

5-[4-(1-tert-Butoxycarbonylamino-1-methylethyl)phenyl]-4-formyl-2-(tetrahydropyran-2-yl)-2H-indazole (Compound 1-6)

Property: white powder
Rf value: 0.46 (n-hexane:ethyl acetate=1:1 (v/v))
Mass spectrum (EI, m/z): 463 (M$^+$)
$^1$H-NMR spectrum (CDCl$_3$, δppm): 1.40 (brs, 9H), 1.62-1.84 (m, 9H), 2.02-2.37 (m, 3H), 3.75-3.87 (m, 1H), 4.11-

4.19 (m, 1H), 4.98 (brs, 1H), 5.70-5.77 (m, 1H), 7.35-7.44 (m, 3H), 7.48-7.54 (m, 2H), 8.02 (dd, J1=9.0 Hz, J2=0.9 Hz, 1H), 8.95 (d, J=0.9 Hz, 1H), 10.06 (s, 1H)

5-[4-(1-tert-Butoxycarbonylamino-1-methylethyl) phenyl]-4-methylcarbonyl-2-(tetrahydropyran-2-yl)-2H-indazole (Compound 1-7)

Property: pale yellow powder
Melting point: 196 to 198° C.
Rf value: 0.46 (n-hexane:ethyl acetate=1:1 (v/v))
Mass spectrum (EI, m/z): 477 ($M^+$)
$^1$H-NMR spectrum (CDCl$_3$, δppm): 1.37 (brs, 9H), 1.58-1.86 (m, 9H), 1.94 (s, 3H), 2.01-2.35 (m, 3H), 3.74-3.83 (m, 1H), 4.10-4.17 (m, 1H), 4.97 (brs, 1H), 5.66-5.71 (m, 1H), 7.33-7.39 (m, 3H), 7.45-7.51 (m, 2H), 7.86 (dd, J1=8.8 Hz, J2=0.9 Hz, 1H), 8.42 (d, J=0.9 Hz, 1H)

4-Benzyloxy-5-[4-(1-tert-butoxycarbonylamino-1-methylethyl)phenyl]-1-(tetrahydropyran-2-yl)-1H-indazole (Compound 1-8)

Rf value: 0.40 (n-hexane:ethyl acetate=2:1 (v/v))
Mass spectrum (EI, m/z): 541 ($M^+$)
$^1$H-NMR spectrum (CDCl$_3$, δppm): 1.39 (brs, 9H), 1.60-1.81 (m, 9H), 2.04-2.17 (m, 2H), 2.51-2.63 (m, 1H), 3.73-3.80 (m, 1H), 4.03-4.14 (m, 1H), 4.86 (brs, 1H), 4.97 (s, 2H), 5.68-5.73 (m, 1H), 7.18-7.31 (m, 5H), 7.35 (dd, J1=8.5 Hz, J2=0.7 Hz, 1H), 7.39-7.46 (m, 3H), 7.51-7.55 (m, 2H), 8.07 (d, J=0.7 Hz, 1H)

5-[4-(1-tert-Butoxycarbonylamino-1-methylethyl) phenyl]-4-methoxy-2-(tetrahydropyran-2-yl)-2H-indazole (Compound 1-9)

Rf value: 0.44 (n-hexane:ethyl acetate=1:1 (v/v))
Mass spectrum (EI, m/z): 465 ($M^+$)
$^1$H-NMR spectrum (CDCl$_3$, δppm): 1.38 (brs, 9H), 1.68-1.82 (m, 9H), 2.04-2.26 (m, 3H), 3.76-3.84 (m, 4H), 4.13-4.18 (m, 1H), 4.94 (brs, 1H), 5.66-5.71 (m, 1H), 7.30 (d, J=8.8 Hz, 1H), 7.42-7.55 (m, 5H), 8.30 (d, J=1.0 Hz, 1H)

Example 2

Synthesis of 5-[4-(1-tert-butoxycarbonylamino-1-methylethyl)phenyl]-1H-indazole (Compound 2)

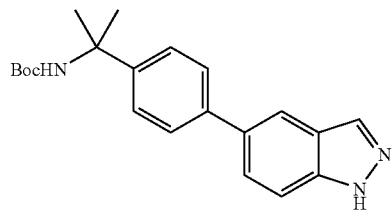

5 ml of tetrahydrofuran, 5 ml of methanol and 0.5 ml of a 1 N aqueous solution of sodium hydroxide were added to 350 mg (0.89 mmol) of 1-acetyl-5-[4-(1-tert-butoxycarbonylamino-1-methylethyl)phenyl]-1H-indazole (Compound 1-1) and the mixture was stirred at room temperature for 10 minutes.

After the reaction was completed, the reaction solution was poured into 50 ml of water and the mixture was extracted with each 50 ml of chloroform for three times. The organic layer was successively washed with water and a saturated aqueous solution of sodium chloride, dried over anhydrous magnesium sulfate and concentrated under reduced pressure. 5 ml of methanol and 20 ml of diethyl ether were added to the resulting crude crystals to wash the crystals, whereby 209 mg of the title compound was obtained as white powder (yield: 67%).

Rf value: 0.32 (n-hexane:ethyl acetate=1:1 (v/v))
Mass spectrum (CI, m/z): 352 ($M^+$+1)
$^1$H-NMR spectrum (DMSO-d$_6$, δppm): 1.35 (brs, 9H), 1.53 (s, 6H), 7.21 (brs, 1H), 7.40 (d, J=8.5 Hz, 2H), 7.59-7.63 (m, 3H), 7.66 (dd, J1=8.8 Hz, J2=1.7 Hz, 1H), 8.00 (dd, J1=1.7 Hz, J2=1.0 Hz, 1H), 8.11 (d, J=1.0 Hz, 1H), 13.10 (brs, 1H)

Example 3

Synthesis of 5-[4-(1-tert-butoxycarbonylamino-1-methylethyl)phenyl]-3-methoxycarbonyl-1H-indazole (Compound 3-1)

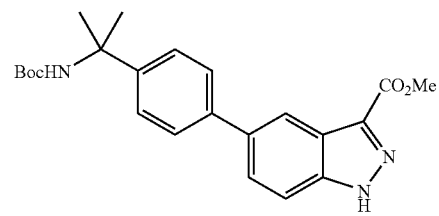

2 ml of tetrahydrofuran, 2 ml of methanol and 0.2 ml of a 1 N aqueous solution of sodium hydroxide were added to 70 mg (0.14 mmol) of 1-tert-butoxycarbonyl-5-[4-(1-tert-butoxycarbonylamino-1-methylethyl)phenyl]-3-methoxycarbonyl-1H-indazole (Compound 1-2) and the mixture was stirred at room temperature for 30 minutes.

After the reaction was completed, the reaction solution was poured into 50 ml of chloroform and the mixture was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure, whereby 51 mg of the title compound was obtained as white powder (yield: 91%).

Rf value: 0.24 (n-hexane:ethyl acetate=1:1 (v/v))
Mass spectrum (CI, m/z): 410 ($M^+$+1)
$^1$H-NMR spectrum (CDCl$_3$, δppm): 1.42 (brs, 9H), 1.68 (s, 6H), (s, 3H), 5.05 (brs, 1H), 7.45-7.61 (m, 6H), 8.38-41 (m, 1H), 11.09 (brs, 1H)

Hereinafter, Compound 3-2 was produced in accordance with the production method for the Compound 3-1.

5-[4-(1-tert-Butoxycarbonylamino-1-methylethyl) phenyl]-3-formyl-1H-indazole (Compound 3-2)

Rf value: 0.45 (n-hexane:ethyl acetate=1:1 (v/v))
Mass spectrum (CI, m/z): 380 ($M^+$+1)
$^1$H-NMR spectrum (CDCl$_3$, δppm): 1.44 (brs, 9H), 1.68 (s, 6H), (brs, 1H), 7.41-7.48 (m, 6H), 8.45-8.47 (m, 1H), (s, 1H), 11.26 (brs, 1H)

Example 4

Synthesis of 5-[4-(1-amino-1-methylethyl)phenyl]-1H-indazole dihydrochloride (Compound 4-1)

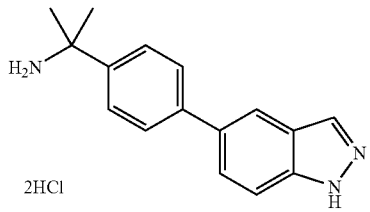

4 ml of methanol and 8 ml of a 4 N solution of hydrogen chloride in 1,4-dioxane were added to 285 mg (0.63 mmol) of 5-[4-(1-tert-butoxycarbonylamino-1-methylethyl)phenyl]-1 h-indazole (Compound 2) and the mixture was stirred in argon stream at room temperature for 2.5 hours.

After the reaction was completed, the reaction solution was concentrated under reduced pressure. 1.5 ml of methanol was added thereto and the resulting residue was dissolved therein, 10 ml of 1,4-dioxane was added thereto and the resulting solid was collected by filtration and washed with diethyl ether, whereby 130 mg of the title compound was obtained as white powder (yield: 63%).

Melting point: 268 to 270° C. (decomposition)
Rf value: 0.30 (chloroform:methanol: 28% aqueous ammonia=5:1:0.01 (v/v/v))
Mass spectrum (CI, m/z): 252 ($M^+$+1)
$^1$H-NMR spectrum (DMSO-$d_6$, δppm): 1.68 (s, 6H), 7.62-7.66 (m, 3H), 7.69 (dd, J1=8.8 Hz, J2=1.7 Hz, 1H), 7.77 (d, J=8.8 Hz, 2H), 8.06 (dd, J1=1.7 Hz, J2=1.0 Hz, 1H), 8.14 (d, J=1.0 Hz, 1H), 8.67 (brs, 3H)

Hereinafter, Compounds 4-2 to 4-9 were produced in accordance with the production method for the Compound 4-1.

5-[4-(1-Amino-1-methylethyl)phenyl]-4-nitro-1H-indazole monohydrochloride (Compound 4-2)

Melting point: 255 to 261° C. (decomposition)
Rf value: 0.33 (chloroform:methanol: 28% aqueous ammonia=5:1:0.01 (v/v/v))
IR spectrum (KBr, cm$^{-1}$): 1516, 1332
Mass spectrum (CI, m/z): 297 ($M^+$+1)
$^1$H-NMR spectrum (DMSO-$d_6$, δppm): 1.69 (s, 6H), 7.47-7.51 (m, 3H), 7.65-7.68 (m, 2H), 8.00 (dd, J1=8.5 Hz, J2=1.0 Hz, 1H), 8.31 (d, J=1.0 Hz, 1H), 8.66 (brs, 3H), 13.93 (brs, 1H)

5-[4-(1-Amino-1-methylethyl)phenyl]-4-dimethylamino-1H-indazole trihydrochloride (Compound 4-3)

Melting point: 219 to 224° C. (decomposition)
Rf value: 0.46 (chloroform:methanol: 28% aqueous ammonia=5:1:0.01 (v/v/v))
Mass spectrum (CI, m/z): 295 ($M^+$+1)
$^1$H-NMR spectrum (DMSO-$d_6$, δppm): 1.69 (s, 6H), 2.84 (s, 6H), 7.14 (d, J=8.5 Hz, 1H), 7.21-7.25 (m, 1H), 7.49 (d, J=8.5 Hz, 2H), 7.61 (d, J=8.5 Hz, 2H), 8.34 (s, 1H), 8.64 (brs, 3H)

5-[5-(1-Amino-1-methylethyl)pyridin-2-yl]-4-cyclopropyl-1H-indazole trihydrochloride (Compound 4-4)

Melting point: 209 to 213° C. (decomposition)
Rf value: 0.47 (chloroform:methanol: 28% aqueous ammonia=5:1:0.01 (v/v/v))
Mass spectrum (CI, m/z): 293 ($M^+$+1)
$^1$H-NMR spectrum (DMSO-$d_6$, δppm): 0.47-0.53 (m, 2H), 0.86-0.93 (m, 2H), 1.78 (s, 6H), 2.41-2.50 (m, 1H), 7.47 (d, J=8.5 Hz, 1H), 7.52-7.56 (m, 1H), 8.02 (d, J=8.3 Hz, 1H), 8.25 (d, J=1.0 Hz, 1H), 8.43-8.46 (m, 1H), 8.99-9.10 (m, 4H)

5-[4-(1-Amino-1-methylethyl)phenyl]-4-cyano-1H-indazole monohydrochloride (Compound 4-5)

Property: white powder
Melting point: 270 to 272° C.
Rf value: 0.38 (chloroform:methanol: 28% aqueous ammonia=10:1:0.1 (v/v/v))
Mass spectrum (CI, m/z): 277 ($M^+$+1)
$^1$H-NMR spectrum (DMSO-$d_6$, δppm): 1.71 (s, 6H), 7.61 (d, J=8.8 Hz, 1H), 7.69-7.81 (m, 4H), 8.02 (d, J=8.8 Hz, 1H), 8.31 (s, 1H), 8.68-8.85 (m, 3H), 13.85 (brs, 1H)

5-[4-(1-Amino-1-methylethyl)phenyl]-4-(pyrrolidin-1-yl)-1H-indazole trihydrochloride (Compound 4-6)

Melting point: 218 to 224° C. (decomposition)
Rf value: 0.44 (chloroform:methanol: 28% aqueous ammonia=5:1:0.01 (v/v/v))
Mass spectrum (EI, m/z): 320 ($M^+$)
$^1$H-NMR spectrum (DMSO-$d_6$, δppm): 1.67 (s, 6H), 1.71-1.80 (m, 4H), 3.18-3.34 (m, 4H), 6.91 (d, J=8.2 Hz, 1H), 7.01 (d, J=8.2 Hz, 1H), 7.41 (d, J=8.4 Hz, 2H), 7.54 (d, J=8.4 Hz, 2H), 8.30 (s, 1H), 8.57 (brs, 3H)

5-[4-(1-Amino-1-methylethyl)phenyl]-4-methoxy-1H-indazole dihydrochloride (Compound 4-7)

Melting point: 258 to 261° C. (decomposition)
Rf value: 0.34 (chloroform:methanol: 28% aqueous, ammonia=5:1:0.01 (v/v/v))
Mass spectrum (CI, m/z): 282 ($M^+$+1)
$^1$H-NMR spectrum (DMSO-$d_6$, δppm): 1.68 (s, 6H), 4.07 (s, 3H), 7.24 (dd, J1=8.5 Hz, J2=0.7 Hz, 1H), 7.29 (d, J=8.5 Hz, 1H), 7.53-7.62 (m, 4H), 8.37 (d, J=0.7 Hz, 1H), 8.61-8.73 (m, 3H)

5-[5-(1-Amino-1-methylethyl)pyridin-2-yl]-4-difluoromethoxy-1H-indazole trihydrochloride (Compound 4-8)

Melting point: 170 to 173° C.
Rf value: 0.37 (chloroform:methanol: 28% aqueous ammonia=5:1:0.01 (v/v/v))
Mass spectrum (CI, m/z): 319 ($M^+$+1)
$^1$H-NMR spectrum (DMSO-$d_6$, δppm): 1.73 (s, 6H), 7.31 (t, $^2J_{F-H}$=73.7 Hz, 1H), 7.60 (dd, J1=8.8 Hz, J2=0.7 Hz, 1H), 7.78 (d, J=8.8 Hz, 1H), 7.88 (dd, J1=8.3 Hz, J2=0.7 Hz, 1H), 8.10 (dd, J1=8.3 Hz, J2=2.4 Hz, 1H), 8.18 (d, J=0.7 Hz, 1H), 8.69 (brs, 3H), 8.90 (dd, J1=2.4 Hz, J2=0.7 Hz, 1H)

5-[4-(1-Amino-1-methylethyl)phenyl]-4-(isoxazol-5-yl)-1H-indazole dihydrochloride (Compound 4-9)

Property: pale yellow powder
Melting point: 256 to 258° C. (decomposition)
Rf value: 0.41 (chloroform:methanol: 28% aqueous ammonia=10:1:0.1 (v/v/v))
Mass spectrum (CI, m/z): 319 ($M^+$+1)

$^1$H-NMR spectrum (DMSO-d$_6$, δppm): 1.68 (s, 6H), 6.24 (d, J=2.0 Hz, 1H), 7.31-7.37 (m, 2H), 7.42 (d, J=8.5 Hz, 1H), 7.56-7.62 (m, 2H), 7.79 (dd, J1=8.5 Hz, J2=1.0 Hz, 1H), 8.21 (d, J=1.0 Hz, 1H), 8.59 (d, J=2.0 Hz, 1H), 8.63-8.80 (m, 3H)

Example 5

Synthesis of 4-amino-1-tert-butoxycarbonyl-5-[4-(1-tert-butoxycarbonylamino-1-methylethyl)phenyl]-1H-indazole (Compound 5)

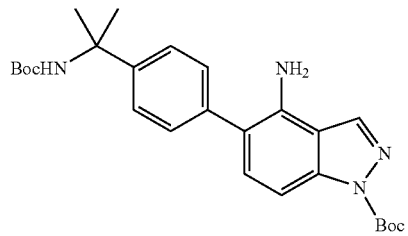

10 ml of 1,4-dioxane and 20 ml of ethanol were added to 336 mg (0.68 mmol) of 1-tert-butoxycarbonyl-5-[4-(1-tert-butoxycarbonylamino-1-methylethyl)phenyl]-4-nitro-1H-indazole (Compound 1-4), then a suspension of 672 mg of 5% palladium-carbon (hydrous) in 10 ml of ethanol was added thereto and the mixture was stirred in a hydrogen atmosphere at room temperature for 1 hour.

After the reaction was completed, the reaction solution was filtered through Celite and the filtrate was concentrated under reduced pressure. The resulting residue was subjected to silica gel column chromatography (eluting solvent: n-hexane:ethyl acetate=2:1 (v/v)) and the fraction containing the desired substance was concentrated under reduced pressure, whereby 225 mg of the title compound was obtained as white powder (yield: 81%).

Rf value: 0.45 (n-hexane:ethyl acetate=1:1 (v/v))
Mass spectrum (FAB, m/z): 466 (M$^+$+1)
$^1$H-NMR spectrum (CDCl$_3$, δppm): 1.40 (brs, 9H), 1.68 (s, 6H), 1.73 (s, 9H), 4.98 (brs, 1H), 7.30 (d, J=8.5 Hz, 1H), 7.40-7.43 (m, 2H), 7.48-7.51 (m, 2H), 7.56 (d, J=8.5 Hz, 1H), 8.14 (s, 1H)

Example 6

Synthesis of 5-[4-(1-tert-butoxycarbonylamino-1-methylethyl)phenyl]-3-hydroxyiminomethyl-1H-indazole (Compound 6-1)

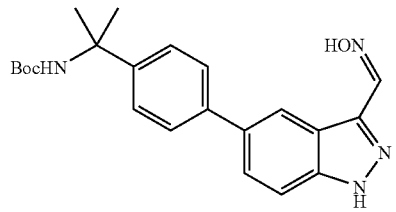

A solution of 194 mg (1.50 mmol) of N,N-diisopropylethylamine in 1 ml of ethanol was added to a solution of 114 mg (0.300 mmol) of 5-[4-(1-tert-butoxycarbonylamino-1-methylethyl)phenyl]-3-formyl-1H-indazole (Compound 3-2) in 25 ml of ethanol in an argon stream with stirring. Then, 83.0 mg (1.29 mmol) of hydroxylamine monohydrochloride was added thereto and the mixture was stirred at room temperature for 7 hours.

After the reaction was completed, the reaction solution was concentrated under reduced pressure, 50 ml of a saturated aqueous solution of ammonium chloride was added thereto and the mixture was extracted with 100 ml of ethyl acetate. The organic layer was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure, whereby 105 mg of the title compound was obtained as white powder (yield: 89%).

Rf value: 0.40 (n-hexane:ethyl acetate=1:1 (v/v))
Mass spectrum (CI, m/z): 395 (M$^+$+1)
$^1$H-NMR spectrum (DMSO-d$_6$, δppm): 1.35 (brs, 9H), 1.53 (s, 6H), 7.19 (brs, 1H), 7.43 (d, J=8.5 Hz, 2H), 7.57 (d, J=8.5 Hz, 2H), 7.64 (dd, J1=8.8 Hz, J2=0.7 Hz, 1H), 7.72 (dd, J1=8.8 Hz, J2=1.7 Hz, 1H), 8.26-8.27 (m, 1H), 8.39 (s, 1H), 11.42 (s, 1H), 13.38 (brs, 1H)

Hereinafter, Compound 6-2 was produced in accordance with the production method for the Compound 6-1.

5-[4-(1-tert-Butoxycarbonylamino-1-methylethyl)phenyl]-4-hydroxyiminomethyl-2-(tetrahydropyran-2-yl)-2H-indazole (Compound 6-2)

Rf value: 0.36 (n-hexane:ethyl acetate=1:1 (v/v))
Mass spectrum (CI, m/z): 479 (M$^+$+1)
$^1$H-NMR spectrum (CDCl$_3$, δppm): 1.39 (brs, 9H), 1.63-1.85 (m, 9H), 2.02-2.13 (m, 1H), 2.18-2.31 (m, 2H), 3.76-3.85 (m, 1H), 4.11-4.19 (m, 1H), 4.96 (brs, 1H), 5.68-5.73 (m, 1H), 7.25 (d, J=8.8 Hz, 1H), 7.29-7.35 (m, 2H), 7.43-7.50 (m, 2H), 7.79 (dd, J1=8.8 Hz, J2=0.9 Hz, 1H), 8.30 (s, 1H), 8.71 (d, J=0.9 Hz, 1H)

Example 7

Synthesis of 5-[4-(1-tert-butoxycarbonylamino-1-methylethyl)phenyl]-3-cyano-1H-indazole (Compound 7-1)

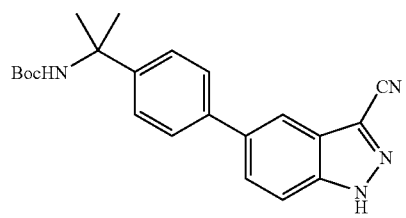

A solution of 220 mg (1.7 mmol) of N,N-diisopropylethylamine in 0.5 ml of tetrahydrofuran and a solution of 240 mg (1.1 mmol) of trifluoroacetic anhydride in 0.5 ml of tetrahydrofuran were added to a solution of 45 mg (0.11 mmol) of 5-[4-(1-tert-butoxycarbonylamino-1-methylethyl)phenyl]-3-hydroxyiminomethyl-1H-indazole (Compound 6-1) in 5 ml of tetrahydrofuran at 0° C. in an argon stream with stirring. The mixture was stirred at 0° C. for 2 hours, a solution of 100 mg (0.77 mmol) of N,N-diisopropylethylamine in 0.5 ml of tetrahydrofuran and a solution of 100 mg (0.48 mmol) of trifluoroacetic anhydride in 0.5 ml of tetrahydrofuran were added thereto and the mixture was stirred at 0° C. for 1 hour. Then, 5 ml of 28% aqueous ammonia was added thereto, a cooling bath was removed to warm up the mixture gradually to room temperature.

After the reaction was completed, the reaction solution was poured into 50 ml of a saturated aqueous solution of ammonium chloride and the mixture was extracted with 50 ml of ethyl acetate. The organic layer was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure, whereby 25 mg of the title compound was obtained as white powder (yield: 58%).

Rf value: 0.43 (n-hexane:ethyl acetate=1:1 (v/v))
Mass spectrum (CI, m/z): 377 (M$^+$+1)
$^1$H-NMR spectrum (DMSO-d$_6$, δppm): 1.35 (brs, 9H), 1.54 (s, 6H), 7.21 (brs, 1H), 7.44 (d, J=8.4 Hz, 2H), 7.71 (d, J=8.4 Hz, 2H), 7.81-7.88 (m, 2H), 8.06-8.07 (m, 1H)

Hereinafter, Compound 7-2 was produced in accordance with the production method for the Compound 7-1.

5-[4-(1-tert-Butoxycarbonylamino-1-methylethyl)phenyl]-4-cyano-2-(tetrahydropyran-2-yl)-2H-indazole (Compound 7-2)

Rf value: 0.55 (n-hexane:ethyl acetate=1:1 (v/v))
Mass spectrum (EI, m/z): 460 (M$^+$)
$^1$H-NMR spectrum (CDCl$_3$, δppm): 1.39 (brs, 9H), 1.63-1.88 (m, 9H), 2.01-2.32 (m, 3H), 3.78-3.87 (m, 1H), 4.12-4.23 (m, 1H), 4.97 (brs, 1H), 5.72-5.77 (m, 1H), 7.45 (d, J=9.0 Hz, 1H), 7.50-7.64 (m, 4H), 7.98 (dd, J1=9.0 Hz, J2=0.9 Hz, 1H), 8.41 (d, J=0.9 Hz, 1H)

Example 8

Synthesis of 1-tert-butoxycarbonyl-5-[4-(1-tert-butoxycarbonylamino-1-methylethyl)phenyl]-4-dimethylamino-1H-indazole (Compound 8)

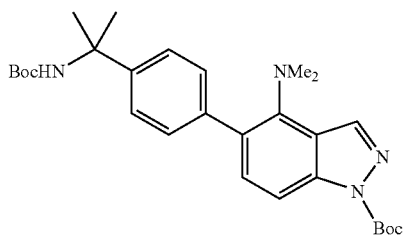

4.00 ml (50.6 mmol) of a 38% aqueous solution of formaldehyde and a suspension of 940 mg of 5% palladium-carbon (hydrous) in 10 ml of ethyl acetate were added to a solution of 470 mg (1.01 mmol) of 4-amino-1-tert-butoxycarbonyl-5-[4-(1-tert-butoxycarbonylamino-1-methylethyl)phenyl]-1H-indazole (Compound 5) in 60 ml of methanol and the mixture was stirred in a hydrogen atmosphere at room temperature for 4 hours.

After the reaction was completed, the reaction solution was filtered and the filtrate was concentrated under reduced pressure. 200 ml of ethyl acetate was added to the resulting residue, the mixture was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=4:1 (v/v)) and the fraction containing the desired substance was concentrated under reduced pressure, whereby 408 mg of the title compound was obtained as white powder (yield: 82%).

Rf value: 0.44 (n-hexane:ethyl acetate=2:1 (v/v))
Mass spectrum (CI, m/z): 495 (M$^+$+1)
$^1$H-NMR spectrum (CDCl$_3$, δppm): 1.38 (brs, 9H), 1.68 (s, 6H), 1.73 (s, 9H), 2.81 (s, 6H), 4.94 (brs, 1H), 7.34-7.38 (m, 3H), 7.41-7.45 (m, 2H), 7.75-7.78 (m, 1H), 8.35 (d, J=0.7 Hz, 1H)

Example 9

Synthesis of 5-[5-(1-tert-butoxycarbonylamino-1-methylethyl)-pyridin-2-yl]-4-hydroxy-1-(tetrahydropyran-2-yl)-1H-indazole (Compound 9-1)

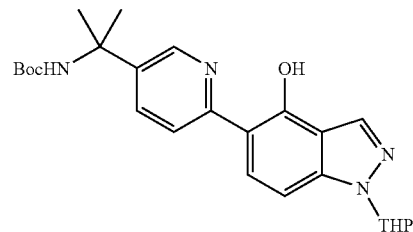

50 ml of tetrahydrofuran and 100 ml of ethanol were added to 7.55 g (13.9 mmol) of 4-benzyloxy-5-[5-(1-tert-butoxycarbonylamino-1-methylethyl)pyridin-2-yl]-1-(tetrahydropyran-2-yl)-1H-indazole (Compound 1-5), then a suspension of 3.32 g of 5% palladium-carbon (hydrous) in 50 ml of ethanol was added thereto and the mixture was stirred in a hydrogen atmosphere at room temperature for 30 minutes.

After the reaction was completed, the reaction solution was filtered through Celite and the filtrate was concentrated under reduced pressure. The resulting residue was dissolved in 20 ml of tetrahydrofuran, 200 ml of n-hexane was added thereto and the resulting solid was collected by filtration, whereby 5.70 g of the title compound was obtained as slightly yellow powder (yield: 91%).

Rf value: 0.45 (n-hexane:ethyl acetate=1:1 (v/v))
Mass spectrum (CI, m/z): 453 (M$^+$+1)
$^1$H-NMR spectrum (CDCl$_3$, δppm): 1.37 (brs, 9H), 1.60-1.85 (m, 9H), 2.05-2.20 (m, 2H), 2.51-2.63 (m, 1H), 3.70-3.79 (m, 1H), 4.01-4.08 (m, 1H), 4.97 (brs, 1H), 5.65-5.70 (m, 1H), 7.06 (dd, J1=8.8 Hz, J2=0.7 Hz, 1H), 7.75-7.86 (m, 3H), 8.24 (d, J=0.7 Hz, 1H), 8.52 (dd, J1=2.2 Hz, J2=1.0 Hz, 1H), 15.84 (brs, 1H)

Hereinafter, Compound 9-2 was produced in accordance with the production method for the Compound 9-1.

5-[4-(1-tert-Butoxycarbonylamino-1-methylethyl)phenyl]-4-hydroxy-1-(tetrahydropyran-2-yl)-1H-indazole (Compound 9-2)

Rf value: 0.24 (n-hexane:ethyl acetate=1:1 (v/v))
Mass spectrum (CI, m/z): 452 (M$^+$+1)
$^1$H-NMR spectrum (DMSO-d$_6$, δppm): 1.35 (brs, 9H), 1.48-1.58 (m, 8H), 1.73-1.79 (m, 1H), 1.90-2.06 (m, 2H), 2.34-2.49 (m, 1H), 3.68-3.77 (m, 1H), 3.87-3.92 (m, 1H), 5.73-5.78 (m, 1H), 7.12-7.21 (m, 2H), 7.29-7.36 (m, 3H), 7.49 (d, J=8.5 Hz, 2H), 8.30 (s, 1H), 10.07 (brs, 1H)

Example 10

Synthesis of 5-[5-(1-tert-butoxycarbonylamino-1-methylethyl)pyridin-2-yl]-1-(tetrahydropyran-2-yl)-4-trifluoromethanesulfonyloxy-1H-indazole (Compound 10)

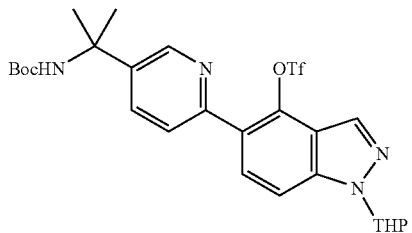

A solution of 1.61 ml (9.57 mmol) of trifluoromethanesulfonic anhydride in 15 ml of methylene chloride was added dropwise to a solution of 2.26 g (4.99 mmol) of 5-[5-(1-tert-butoxycarbonylamino-1-methylethyl)pyridin-2-yl]-4-hydroxy-1-(tetrahydropyran-2-yl)-1H-indazole (Compound 9-1) and 4.35 ml (23.9 mmol) of N,N-diisoproylethylamine in 50 ml of methylene chloride at 0° C. over 30 minutes and the mixture was stirred for 20 minutes.

After the reaction was completed, the reaction solution was poured into 40 ml of a saturated aqueous solution of sodium hydrogen carbonate and the mixture was extracted with 100 ml of chloroform. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=4:1 to 2:1 (v/v)) and the fraction containing the desired substance was concentrated under reduced pressure, whereby 2.80 g of the title compound was obtained as a slightly yellow foamy substance (yield: 96%).

Rf value: 0.41 (n-hexane:ethyl acetate=1:1 (v/v))
Mass spectrum (CI, m/z): 585 (M$^+$+1)
$^1$H-NMR spectrum (CDCl$_3$, δppm): 1.38 (brs, 9H), 1.60-1.84 (m, 9H), 2.09-2.21 (m, 2H), 2.50-2.61 (m, 1H), 3.72-3.81 (m, 1H), 3.99-4.05 (m, 1H), 5.01 (brs, 1H), 5.76-5.80 (m, 1H), 7.59 (d, J=8.5 Hz, 1H), 7.71 (dd, J1=8.7 Hz, J2=0.9 Hz, 1H), 7.77-7.82 (m, 2H), 8.16 (s, 1H), 8.80 (dd, J1=2.6 Hz, J2=0.9 Hz, 1H)

Example 11

Synthesis of 5-[5-(1-tert-butoxycarbonylamino-1-methylethyl)pyridin-2-yl]-4-cyclopropyl-1-(tetrahydropyran-2-yl)-1H-indazole (Compound 11)

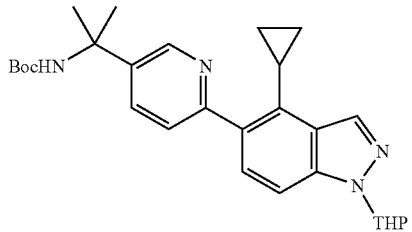

206 mg (2.40 mmol) of cyclopropylboronic acid, 556 mg (2.40 mmol) of silver (I) oxide, 365 mg (2.40 mmol) of cesium fluoride, 185 mg (0.160 mmol) of tetrakis (triphenylphosphine)palladium and 20 ml of 1,2-dimethoxyethane were added to 468 mg (0.801 mmol) of 5-[5-(1-tert-butoxycarbonylamino-1-methylethyl)pyridin-2-yl]-1-(tetrahydropyran-2-yl)-4-trifluoromethanesulfonyloxy-1H-indazole (Compound 10) and the mixture was stirred in an argon stream for 30 minutes under a condition of heating to reflux.

After the reaction was completed, the reaction solution was poured into 100 ml of water and the mixture was extracted with 100 ml of ethyl acetate. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=3:1 (v/v)) and the fraction containing the desired substance was concentrated under reduced pressure, whereby 260 mg of the title compound was obtained as slightly orange powder (yield: 68%).

Rf value: 0.33 (n-hexane:ethyl acetate=1:1 (v/v))
Mass spectrum (CI, m/z): 477 (M$^+$+1)
$^1$H-NMR spectrum (CDCl$_3$, δppm): 0.55-0.61 (m, 2H), 0.82-0.90 (m, 2H), 1.37 (brs, 9H), 1.60-1.86 (m, 9H), 2.06-2.21 (m, 2H), 2.30-2.36 (m, 1H), 2.54-2.65 (m, 1H), 3.70-3.79 (m, 1H), 4.02-4.06 (m, 1H), 4.99 (brs, 1H), 5.70-5.75 (m, 1H), 7.46-7.57 (m, 3H), 7.74 (dd, J1=8.3 Hz, J2=2.6 Hz, 1H), 8.20 (s, 1H), 8.76 (dd, J1=2.6 Hz, J2=0.7 Hz, 1H)

Example 12

Synthesis of 1-tert-butoxycarbonyl-5-[4-(1-tert-butoxycarbonylamino-1-methylethyl)phenyl]-4-(piperidin-1-yl)-1H-indazole (Compound 12-1)

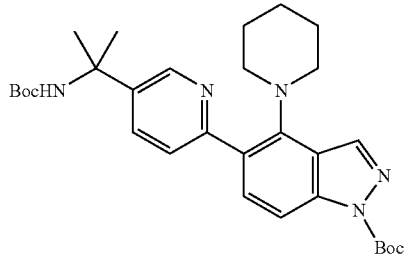

A suspension of 320 mg of 5% palladium-carbon (hydrous) in 3 ml of ethanol and 6.87 ml of a 50% aqueous solution of glutaraldehyde were added to a solution of 160 mg (0.343 mmol) of 4-amino-1-tert-butoxycarbonyl-5-[4-(1-tert-butoxycarbonylamino-1-methylethyl)phenyl]-1H-indazole (Compound 5) in 30 ml of ethanol and the mixture was stirred in a hydrogen atmosphere at room temperature for 5 hours. Then, 3.44 ml of a 50% aqueous solution of glutaraldehyde was added thereto and the mixture was stirred in a hydrogen atmosphere at room temperature for 2 hours.

After the reaction was completed, the reaction solution was filtered through Celite and the filtrate was concentrated under reduced pressure. Water was added to the resulting residue and the resulting precipitate was collected by filtration and washed with water. The resulting powder was subjected to silica gel column chromatography (eluting solvent: n-hexane:ethyl acetate=6:1 (v/v)) and the fraction containing the desired substance was concentrated under reduced pressure, whereby 163 mg of the title compound was obtained as a white foamy substance (yield: 89%).

Rf value: 0.38 (n-hexane:ethyl acetate=2:1 (v/v))
Mass spectrum (CI, m/z): 535 (M$^+$+1)

$^1$H-NMR spectrum (CDCl$_3$, δppm): 1.27-1.54 (m, 15H), 1.68 (s, 6H), 1.73 (s, 9H), 3.05-3.10 (m, 4H), 4.97 (brs, 1H), 7.35 (d, J=8.5 Hz, 1H), 7.40-7.45 (m, 4H), 7.79 (d, J=8.5 Hz, 1H), 8.34 (s, 1H)

Hereinafter, Compound 12-2 was produced in accordance with the production method for the Compound 12-1.

Incidentally, succinaldehyde used in the synthesis of the Compound 12-2 was synthesized by referring to A. R. Katritzky, et al., J. Org. Chem., vol. 65, p. 3683 (2000).

1-tert-Butoxycarbonyl-5-[4-(1-tert-butoxycarbonylamino-1-methylethyl)phenyl]-4-(pyrrolidin-1-yl)-1H-indazole (Compound 12-2)

Rf value: 0.46 (n-hexane:ethyl acetate=2:1 (v/v))

Mass spectrum (CI, m/z): 521 (M$^+$+1)

$^1$H-NMR spectrum (CDCl$_3$, δppm): 1.37 (brs, 9H), 1.67 (s, 6H), 1.72 (s, 9H), 1.77-1.82 (m, 4H), 3.23-3.28 (m, 4H), 4.94 (brs, 1H), 7.25-7.40 (m, 5H), 7.58-7.62 (m, 1H), 8.41 (d, J=0.7 Hz, 1H)

Example 13

Synthesis of 5-[4-(1-tert-butoxycarbonylamino-1-methylethyl)phenyl]-4-difluoromethoxy-1-(tetrahydropyran-2-yl)-1H-indazole (Compound 13-1)

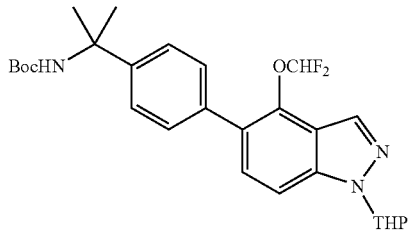

1.47 g (4.51 mmol) of cesium carbonate and 458 mg (3.00 mmol) of sodium chlorodifluoroacetate were added to a solution of 680 mg (1.50 mmol) of 5-[4-(1-tert-butoxycarbonylamino-1-methylethyl)phenyl]-4-hydroxy-1-(tetrahydropyran-2-yl)-1H-indazole (Compound 9-2) in 10 ml of N,N-dimethylformamide, and the mixture was stirred in an argon stream at 100° C. for 45 minutes.

After the reaction was completed, the reaction solution was poured into 50 ml of water and the mixture was extracted with 50 ml of toluene. The organic layer was successively washed with water and a saturated aqueous solution of sodium chloride, dried over anhydrous magnesium sulfate and concentrated under reduced pressure. The resulting residue was subjected to silica gel column chromatography (eluting solvent: n-hexane:ethyl acetate=4:1 (v/v)) and the fraction containing the desired substance was concentrated under reduced pressure, whereby 343 mg of the title compound was obtained as white powder (yield: 46%).

Rf value: 0.46 (n-hexane:ethyl acetate=2:1 (v/v))

Mass spectrum (EI, m/z): 501 (M$^+$)

$^1$H-NMR spectrum (DMSO-d$_6$, δppm): 1.35 (brs, 9H), 1.48-1.85 (m, 9H), 1.95-2.12 (m, 2H), 2.34-2.57 (m, 1H), 3.72-3.82 (m, 1H), 3.86-3.94 (m, 1H), 5.89-5.95 (m, 1H), 7.10 (t, $^2J_{F-H}$=74.0 Hz, 1H), 7.18 (brs, 1H), 7.37-7.48 (m, 4H), 7.49 (d, J=8.8 Hz, 1H), 7.75 (d, J=8.8 Hz, 1H), 8.15 (s, 1H)

Hereinafter, Compound 13-2 was produced in accordance with the production method for the Compound 13-1.

5-[5-(1-tert-Butoxycarbonylamino-1-methylethyl)pyridin-2-yl]-4-difluoromethoxy-1-(tetrahydropyran-2-yl)-1H-indazole (Compound 13-2)

Rf value: 0.29 (n-hexane:ethyl acetate=2:1 (v/v))

Mass spectrum (CI, m/z): 503 (M$^+$+1)

$^1$H-NMR spectrum (DMSO-d$_6$, δppm): 1.34 (brs, 9H), 1.50-1.86 (m, 9H), 1.96-2.12 (m, 2H), 2.34-2.53 (m, 1H), 3.72-3.83 (m, 1H), 3.86-3.95 (m, 1H), 5.89-5.96 (m, 1H), 7.26 (t, $^2J_{F-H}$=74.0 Hz, 1H), 7.33 (brs, 1H), 7.72 (dd, J1=8.5 Hz, J2=0.7 Hz, 1H), 7.76-7.88 (m, 3H), 8.18 (s, 1H), 8.66 (dd, J1=2.4 Hz, J2=0.7 Hz, 1H)

Example 14

Synthesis of 5-[4-(1-tert-butoxycarbonylamino-1-methylethyl)phenyl]-4-(3-dimethylaminoacryloyl)-2-(tetrahydropyran-2-yl)-2H-indazole (Compound 14)

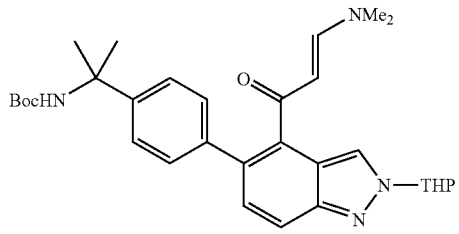

2.0 ml (15 mmol) of N,N-dimethylformamide dimethyl acetal was added to a solution of 500 mg (1.05 mmol) of 5-[4-(1-tert-butoxycarbonylamino-1-methylethyl)phenyl]-4-methylcarbonyl-2-(tetrahydropyran-2-yl)-2H-indazole (Compound 1-7) in 6 ml of N,N-dimethylformamide in an argon stream and the mixture was stirred at 70° C. for 1.5 hours and then at 100° C. for 4 hours.

After the reaction was completed, the reaction solution was concentrated under reduced pressure, the resulting residue was subjected to silica gel column chromatography (eluting solvent: ethyl acetate) and the fraction containing the desired substance was concentrated under reduced pressure. The resulting residue was dissolved in chloroform and ethyl acetate and n-hexane were added thereto and the resulting solid was collected by filtration, whereby 450 mg of the title compound was obtained as yellow powder (yield: 81%).

Melting point: 191 to 194° C.

Rf value: 0.22 (ethyl acetate)

Mass spectrum (CI, m/z): 533 (M$^+$+1)

$^1$H-NMR spectrum (CDCl$_3$, δppm): 1.39 (brs, 9H), 1.59-1.82 (m, 9H), 1.97-2.11 (m, 1H), 2.14-2.30 (m, 2H), 2.45 (brs, 3H), 2.90 (brs, 3H), 3.73-3.83 (m, 1H), 4.08-4.19 (m, 1H), 4.71-4.80 (m, 1H), 4.94 (brs, 1H), 5.64-5.69 (m, 1H), 7.34 (d, J=8.8 Hz, 1H), 7.35-7.45 (m, 5H), 7.77 (dd, J1=8.8 Hz, J2=1.0 Hz, 1H), 8.38-8.42 (m, 1H)

Example 15

Synthesis of 5-[4-(1-tert-butoxycarbonylamino-1-methylethyl)phenyl]-4-(isoxazol-5-yl)-1H-indazole (Compound 15)

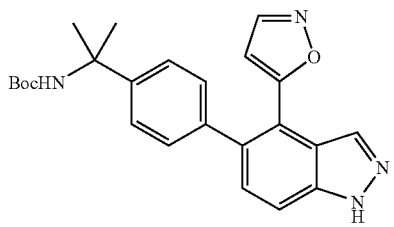

150 mg (2.2 mmol) of hydroxylamine hydrochloride and 150 mg (1.1 mmol) of potassium carbonate were added to a solution of 400 mg (0.75 mmol) of 5-[4-(1-tert-butoxycarbonylamino-1-methylethyl)phenyl]-4-(3-dimethylaminoacryloyl)-2-(tetrahydropyran-2-yl)-2H-indazole (Compound 14) in 5 ml of ethanol in an argon stream and the mixture was stirred for 3 hours under a condition of heating to reflux.

After the reaction was completed, the reaction solution was concentrated under reduced pressure, water was added thereto and the mixture was extracted with ethyl acetate. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=1:1 (v/v)) and the fraction containing the desired substance was concentrated under reduced pressure, whereby 300 mg of the title compound was obtained as a pale yellow foamy substance (yield: 95%).

Rf value: 0.33 (n-hexane:ethyl acetate=1:1 (v/v))
Mass spectrum (CI, m/z): 419 (M$^+$+1)
$^1$H-NMR spectrum (CDCl$_3$, δppm): 1.39 (brs, 9H), 1.68 (s, 6H), (brs, 1H), 5.48-5.60 (m, 1H), 7.21-7.28 (m, 2H), 7.40 (d, J=8.5 Hz, 1H), 7.41-7.48 (m, 2H), 7.55-7.62 (m, 1H), (d, J=2.0 Hz, 1H), 8.57 (s, 1H), 10.41 (brs, 1H)

Preparation Examples

Hereinafter, general preparation examples containing the indazole derivative according to the present invention will be shown.

1) Tablet

| Formulation 1 (in 100 mg) | |
|---|---|
| Indazole derivative | 1 mg |
| Lactose | 66.4 mg |
| Cornstarch | 20 mg |
| Carxboxymethyl cellulose calcium | 6 mg |
| Hydroxypropyl cellulose | 4 mg |
| Magnesium stearate | 0.6 mg |

The tablet having the above formulation is coated with 2 mg of a coating agent (a common coating agent such as hydroxypropylmethyl cellulose, macrogol or a silicone resin), whereby a desired coated tablet is obtained. Further, a desired tablet can be obtained by appropriately changing the kind and/or amount of the indazole derivative and/or additives.

2) Capsule

| Formulation 2 (in 150 mg) | |
|---|---|
| Indazole derivative | 5 mg |
| Lactose | 145 mg |

A desired capsule can be obtained by appropriately changing the mixing ratio of the indazole derivative to lactose.

3) Eye drop

| Formulation 3 (in 100 ml) | |
|---|---|
| Indazole derivative | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the kind and/or amount of the indazole derivative and/or additives.

[Pharmacological Test]

In order to find a new medicinal use of an indazole derivative, an effect of the indazole derivative on protecting retinal neuronal cells against glutamate-induced retinal neuronal cell death was evaluated and studied by using rat fetal retinal neuronal cells.

Incidentally, Compounds 4-2 to 4-9 were used as the test compounds.

(1) Isolation Culture of Retinal Neuronal Cells

A pregnant Wistar rat was subjected to laparotomy under systemic anesthesia, and the uterus was transferred to a dish containing Hanks's balanced salt solution (HBSS). From the uterus, rat fetuses were isolated, and the eyeballs of the rat fetuses were taken out. The retina was isolated from the eyeballs under a stereoscopic microscope and cut into pieces with a surgical knife. Then, the retina was further broken down to the cellular level and passed through a nylon mesh (No. 305, manufactured by NBC Industries Co., Ltd.) to remove cell aggregates, and then, the resulting filtrate was centrifuged at 1000 rpm for 4 minutes. The supernatant was removed, and an appropriate amount of a modified Eagle's medium (MEM) containing 10% fetal bovine serum (FBS) was added to the remaining cells to suspend them. After the cell number was counted with a hemocytometer, an MEM medium containing 10% FBS was added thereto, whereby a cell suspension with a cell density of 0.8×10$^6$ cells/mL was prepared. The cell suspension was inoculated in an amount of 80 μL each into polyethylenimine-coated plastic discs, and the discs were allowed to stand in an incubator (37° C., 5% CO$_2$). The day of cell inoculation was designated as day 1 of culture, and medium replacement was carried out on even number days. Incidentally, up to day 4, a MEM medium containing 10% FBS was used, and on day 8, a MEM medium containing 10% horse serum (HS) was used. Incidentally, on day 6, a medium containing cytarabine (Ara-C) (1.5×10$^{-5}$ M in a MEM medium containing 10% FBS) was used for removing proliferative cells.

(2) Preparation of Serum-Free MEM Medium Containing Test Compound and Glutamate

Each of the test compounds was dissolved in a serum-free MEM medium supplemented with glutamate (1 mM), whereby a serum-free MEM medium containing glutamate and the test compound at 10 μM was prepared.

(3) Evaluation of Cell Death

On day 9 of culture, the plastic discs in which cells were inoculated and cultured were transferred to a serum-free MEM medium and incubated for 24 hours (37° C., 5% $CO_2$). On day 10 of culture, the plastic discs in which cells were inoculated and cultured were transferred to the serum-free MEM medium containing the test compound and glutamate and incubated for 10 minutes, then, transferred to a serum-free MEM medium and incubated for 1 hour (37° C., 5% $CO_2$). The cells were stained with a 1.5% trypan blue solution for 10 minutes, and fixed by adding a 10% formalin fixative solution thereto. After the cells were washed with a physiological saline solution, stained cells and unstained cells were counted under an inverted microscope (one group consisting of 3 to 5 cases).

Incidentally, a group in which the same test as described above was carried out except that a serum-free MEM medium containing glutamate was used instead of the above-mentioned serum-free MEM medium containing the test compound and glutamate was designated as a vehicle addition group.

Further, a group in which the same test as described above was carried out except that a serum-free MEM medium not containing glutamate was used instead of the above-mentioned serum-free MEM medium containing the test compound and glutamate was designated as a glutamate-untreated group.

The survival rates of vehicle addition group and test compound addition group were calculated based on the following calculation equation. Further, the ratio of the survival rate of test compound addition group to the survival rate of vehicle addition group (survival rate ratio: %) was calculated, and an effect of the test compound on protecting a retinal neuronal cell was evaluated.

Survival rate (%)={(unstained cell number)/
(unstained cell number+stained cell number)}×
100

(4) Results and Discussion

Compared with the glutamate-untreated group, about 35 to 55% retinal neuronal cell death was observed in the vehicle addition group. When the ratio of the survival rate (survival rate ratio) of each group in which the serum-free MEM medium containing glutamate and the test compound at 10 μM was used as the medium relative to the survival rate of this vehicle addition group was calculated, as shown in FIG. 1, the survival rate ratio of test compound group was 100% or higher, and the glutamate-induced retinal neuronal cell death was inhibited. In this way, an effect of the test compound on protecting a retinal neuronal cell was confirmed.

BRIEF DESCRIPTION OF THE DRAWING

FIG. 1 is a graph showing the survival rate ratios of test compound addition groups when the survival rate of vehicle addition group after glutamate was added was taken as 100%.

The invention claimed is:

1. A method for treating a disease associated with damage to a retinal neuronal cell selected from the group consisting of abnormal visual field, retinal vascular occlusion, diabetic retinopathy, ischemic optic neuropathy, macular degeneration, retinitis pigmentosa and Leber's disease comprising administering to a patient in need thereof a pharmaceutically effective amount of a compound represented by the following formula (1) or a salt thereof:

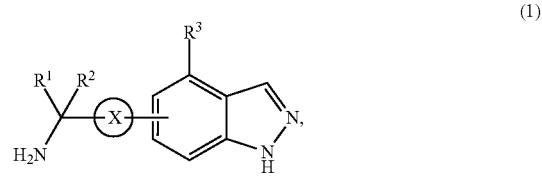

wherein the ring X represents a benzene ring or a pyridine ring;

$R^1$ and $R^2$ are the same or different and represent a hydrogen atom or an alkyl group or $R^1$ and $R^2$ are joined together to form a cycloalkane ring;

$R^3$ represents a hydroxy group, an alkoxy group, an aryloxy group, a cycloalkyl group, an alkylamino group, an arylamino group, a nitro group, a cyano group or a monocyclic heterocycle; and a cyclic moiety of the benzene ring, the pyridine ring, the cycloalkane ring, the aryloxy group, the cycloalkyl group, the arylamino group or the monocyclic heterocycle are unsubstituted or substituted with one or more substituents selected from the group consisting of a halogen atom, an alkoxy group and an alkyl group; and an alkyl moiety of the alkyl group, the alkoxy group or the alkylamino group are unsubstituted or substituted with one or more substituents selected from the group consisting of a halogen atom and an alkoxy group.

2. The method according to claim 1, wherein in the formula (1), the ring X represents a benzene ring or a pyridine ring; $R^1$ and $R^2$ are the same or different and represent an alkyl group;

$R^3$ represents an alkoxy group, a cycloalkyl group, an alkylamino group, a nitro group, a cyano group or a monocyclic heterocycle; and an alkyl moiety of the alkoxy group is unsubstituted or substituted with one or more halogen atoms.

3. The method according to claim 1, wherein in the formula (1), the ring X represents a benzene ring or a pyridine ring;

$R^1$ and $R^2$ represent a methyl group; and $R^3$ represents a methoxy group, a difluoromethoxy group, cyclopropyl group, a dimethylamino group, a nitro group, a cyano group, a pyrrolidine ring or an isoxazole ring.

4. The method according to claim 1, wherein the compound is selected from the group consisting of 5-[4-(1-amino-1-methylethyl)phenyl]-4-nitro-1H-indazole, 5-[4-(1-amino-1-methylethyl)phenyl]-4-dimethylamino-1H-indazole, 5-[4-(1-amino-1-methylethyl)phenyl]-4-(pyrrolidin-1-yl)-1H-indazole, 5-[4-(1-amino-1-methylethyl)phenyl]-4-methoxy-1H-indazole, 5-[4-(1-amino-1-methylethyl)phenyl]-4-cyano-1H-indazole, 5-[5-(1-amino-1-methylethyl)pyridin-2-yl]-4-difluoromethoxy-1H-indazole, 5-[4-(1-amino-1-methylethyl)phenyl]-4-(isoxazol-5-yl)-1H-indazole, and
5-[5-(1-amino-1-methylethyl)pyridin-2-yl]-4-cyclopropyl-1H-indazole,
or a salt thereof.

5. The method according to claim 1, wherein the retinal neuronal cell is a photoreceptor cell, a bipolar cell, an optic ganglion cell, a horizontal cell or an amacrine cell.

* * * * *